(12) United States Patent
Soukup et al.

(10) Patent No.: US 7,892,186 B2
(45) Date of Patent: Feb. 22, 2011

(54) HANDLE AND ARTICULATOR SYSTEM AND METHOD

(75) Inventors: Thomas M. Soukup, Maple Grove, MN (US); Gregory L. Townsend, Plymouth, MN (US); Mark A. Pederson, Minneapolis, MN (US); William Frank Kuester, III, Blaine, MN (US)

(73) Assignee: Heraeus Materials S.A., Penthalaz (CH)

( * ) Notice: Subject to any disclaimer, the term of this patent is extended or adjusted under 35 U.S.C. 154(b) by 1447 days.

(21) Appl. No.: 11/298,548

(22) Filed: Dec. 9, 2005

(65) Prior Publication Data
US 2007/0135733 A1    Jun. 14, 2007

(51) Int. Cl.
*A61M 25/00*    (2006.01)
*A61B 5/00*    (2006.01)
(52) U.S. Cl. .................................. 600/585; 604/95.04
(58) Field of Classification Search ............. 604/95.04, 604/95.01, 93.01; 600/585
See application file for complete search history.

(56) References Cited

U.S. PATENT DOCUMENTS

| | | | |
|---|---|---|---|
| 2,118,631 A | 5/1938 | Wappler | |
| 3,789,841 A | 2/1974 | Antoshkiw | |
| 3,802,440 A | 4/1974 | Salem | |
| 3,841,308 A | 10/1974 | Tate | |
| 4,020,829 A | 5/1977 | Willson | |
| 4,209,019 A | 6/1980 | Dutcher | |
| 4,215,703 A | 8/1980 | Willson | |
| 4,271,845 A | 6/1981 | Chikashige | |
| 4,323,071 A | 4/1982 | Simpson | 128/343 |
| 4,364,392 A | 12/1982 | Strother | |
| 4,439,185 A | 3/1984 | Lundquist | 604/97 |
| 4,456,017 A | 6/1984 | Miles | |
| 4,468,224 A | 8/1984 | Enzmann | 604/247 |
| 4,516,972 A | 5/1985 | Samson | 604/282 |
| 4,538,622 A | 9/1985 | Samson | 128/772 |
| 4,554,929 A | 11/1985 | Samson | 128/772 |
| 4,582,181 A | 4/1986 | Samson | 128/348.1 |
| 4,616,652 A | 10/1986 | Simpson | 128/344 |
| 4,619,263 A | 10/1986 | Frisbie | 128/344 |

(Continued)

FOREIGN PATENT DOCUMENTS

EP    0534303 A2    3/1993

(Continued)

OTHER PUBLICATIONS

Medtronic Placer™ Model 6232 Steerable Stylet, Premarket Notification document, Medtronic, Inc., 5 pgs.; Jun. 16, 2000.

(Continued)

*Primary Examiner*—Kevin C Sirmons
*Assistant Examiner*—Michael J Anderson
(74) *Attorney, Agent, or Firm*—Dicke, Billig & Czaja, PLLC

(57) ABSTRACT

The invention includes an assembly having a handle for articulating an articulator in an ergonomically improved manner. The handle can be adapted to articulate a distal portion of the articulator when squeezed. The handle can have at least one accessible attachment mechanism useful for reattachably attaching the articulator and the handle during a medical procedure. The invention also includes methods of making and using such a handle.

46 Claims, 23 Drawing Sheets

U.S. PATENT DOCUMENTS

| | | | |
|---|---|---|---|
| 4,638,805 A | 1/1987 | Powell | 128/344 |
| 4,664,113 A | 5/1987 | Frisbie | 128/344 |
| 4,719,924 A | 1/1988 | Crittenden | |
| 4,739,768 A | 4/1988 | Engelson | |
| 4,757,827 A | 7/1988 | Buchbinder | |
| 4,759,748 A | 7/1988 | Reed | |
| 4,802,947 A | 2/1989 | Bartholomew | |
| 4,820,349 A | 4/1989 | Saab | |
| 4,822,345 A | 4/1989 | Danforth | |
| 4,846,174 A | 7/1989 | Willard | |
| 4,869,719 A | 9/1989 | Hogan | |
| 4,874,371 A | 10/1989 | Comben | 604/95 |
| 4,886,067 A | 12/1989 | Palermo | |
| 4,917,102 A | 4/1990 | Miller | |
| 5,060,660 A | 10/1991 | Gambale | |
| 5,151,105 A | 9/1992 | Kwan-Gett | |
| RE34,086 E | 10/1992 | George | |
| 5,273,026 A | 12/1993 | Wilk | |
| 5,282,478 A | 2/1994 | Fleischhaker, Jr. | |
| 5,304,131 A | 4/1994 | Paskar | |
| 5,315,996 A | 5/1994 | Lundquist | |
| 5,322,064 A | 6/1994 | Lundquist | |
| 5,327,906 A | 7/1994 | Fideler | 128/772 |
| 5,333,614 A | 8/1994 | Feiring | |
| 5,338,301 A | 8/1994 | Diaz | |
| 5,341,817 A | 8/1994 | Viera | |
| 5,378,236 A | 1/1995 | Seifert | |
| 5,396,902 A | 3/1995 | Brennen | 128/772 |
| 5,403,292 A | 4/1995 | Ju | |
| 5,409,470 A | 4/1995 | McIntyre | |
| 5,437,288 A | 8/1995 | Schwartz | |
| 5,439,006 A | 8/1995 | Brennen | 128/772 |
| 5,441,483 A | 8/1995 | Avitall | |
| 5,472,425 A | 12/1995 | Teirstein | |
| 5,480,382 A | 1/1996 | Hammerslag | |
| 5,483,952 A * | 1/1996 | Aranyi | 600/131 |
| 5,484,565 A | 1/1996 | Larsen | |
| 5,533,967 A | 7/1996 | Imran | |
| 5,545,151 A | 8/1996 | O'Connor | |
| 5,573,520 A | 11/1996 | Schwartz | |
| 5,599,325 A | 2/1997 | Ju | |
| 5,605,162 A | 2/1997 | Mirzaee | |
| 5,605,543 A | 2/1997 | Swanson | |
| 5,658,264 A | 8/1997 | Samson | |
| 5,662,119 A | 9/1997 | Brennan | |
| 5,674,271 A | 10/1997 | Denker | |
| 5,676,653 A * | 10/1997 | Taylor et al. | 604/95.04 |
| 5,685,306 A | 11/1997 | Davidson | |
| 5,722,425 A | 3/1998 | Bostrom | |
| 5,726,615 A | 3/1998 | Bloom | |
| 5,730,717 A * | 3/1998 | Gelbfish | 604/22 |
| 5,743,876 A | 4/1998 | Swanson | |
| 5,752,915 A | 5/1998 | Neubauer | |
| 5,758,656 A | 6/1998 | Schroeder | |
| 5,762,615 A | 6/1998 | Weier | |
| 5,769,858 A | 6/1998 | Pearson | |
| 5,795,341 A | 8/1998 | Samson | |
| 5,820,591 A | 10/1998 | Thompson | |
| 5,824,031 A | 10/1998 | Cookston | |
| 5,824,173 A | 10/1998 | Fontirroche | |
| 5,833,632 A | 11/1998 | Jacobsen | |
| 5,851,203 A | 12/1998 | van Muiden | |
| 5,853,400 A | 12/1998 | Samson | |
| 5,860,953 A | 1/1999 | Snoke | |
| 5,865,800 A | 2/1999 | Mirarchi | 604/95 |
| 5,873,842 A | 2/1999 | Brennen | 600/585 |
| 5,916,178 A | 6/1999 | Noone | |
| 5,916,194 A | 6/1999 | Jacobsen | |
| 5,922,443 A | 7/1999 | Larsen | |
| 5,938,623 A | 8/1999 | Quiachon | |
| 5,951,471 A | 9/1999 | de la Rama | |
| 5,957,903 A | 9/1999 | Mirzaee | |
| 6,004,279 A | 12/1999 | Crowley | |
| 6,017,319 A | 1/2000 | Jacobsen | |
| 6,022,340 A | 2/2000 | Sepetka | |
| 6,027,462 A | 2/2000 | Greene | |
| 6,033,378 A | 3/2000 | Lundquist | 604/95 |
| 6,033,394 A | 3/2000 | Vidlund | |
| 6,039,743 A | 3/2000 | Quiachon | |
| 6,048,339 A | 4/2000 | Zirps | |
| 6,053,903 A | 4/2000 | Samson | |
| 6,053,904 A | 4/2000 | Scribner | |
| 6,059,739 A | 5/2000 | Baumann | |
| 6,068,623 A | 5/2000 | Zadno-Azizi | |
| 6,106,510 A | 8/2000 | Lunn | |
| 6,113,557 A | 9/2000 | Fagan | |
| 6,132,390 A | 10/2000 | Cookston | |
| 6,152,931 A | 11/2000 | Nadal | |
| 6,183,420 B1 | 2/2001 | Douk | |
| 6,203,506 B1 | 3/2001 | Boström | |
| 6,299,628 B1 | 10/2001 | Harrison | |
| 6,306,106 B1 | 10/2001 | Boyle | |
| 6,308,090 B1 | 10/2001 | Tu | |
| 6,450,975 B1 | 9/2002 | Brennan | |
| 6,450,989 B2 | 9/2002 | Dubrul | |
| 6,533,772 B1 | 3/2003 | Sherts | |
| 6,607,496 B1 * | 8/2003 | Poor et al. | 600/585 |
| 6,613,014 B1 | 9/2003 | Chi | 604/93.01 |
| 6,652,491 B1 | 11/2003 | Walker | |
| 6,652,506 B2 | 11/2003 | Bowe | 604/523 |
| 6,752,800 B1 | 6/2004 | Winston | 604/528 |
| 6,755,794 B2 | 6/2004 | Soukup | 600/585 |
| 6,776,765 B2 | 8/2004 | Soukup | 600/585 |
| 6,802,835 B2 | 10/2004 | Rabiner | 604/528 |
| 6,869,414 B2 | 3/2005 | Simpson | |
| D536,786 S | 2/2007 | Schreiner et al. | |
| 2002/0004638 A1 | 1/2002 | Soukup | |
| 2002/0095147 A1 | 7/2002 | Shadduck | |
| 2002/0133111 A1 | 9/2002 | Shadduck | |
| 2002/0165569 A1 | 11/2002 | Ramzipoor | |
| 2003/0036755 A1 | 2/2003 | Ginn | |
| 2003/0040684 A1 | 2/2003 | Soukup | 600/585 |
| 2003/0225395 A1 | 12/2003 | Griffis | |
| 2004/0015151 A1 | 1/2004 | Chambers | |
| 2004/0059257 A1 | 3/2004 | Gaber | |
| 2004/0102719 A1 | 5/2004 | Keith | 600/585 |
| 2004/0158280 A1 | 8/2004 | Morris | |
| 2005/0027214 A1 | 2/2005 | Murayama | |
| 2005/0059990 A1 | 3/2005 | Ayala | |
| 2005/0070754 A1 | 3/2005 | Nobis | |
| 2005/0094935 A1 | 5/2005 | Hattori | |
| 2005/0256452 A1 | 11/2005 | DeMarchi | |
| 2005/0283183 A1 | 12/2005 | Tran | |

FOREIGN PATENT DOCUMENTS

| | | |
|---|---|---|
| EP | 0 739 641 A1 | 10/1996 |
| EP | 1 459 703 A1 | 9/2004 |
| WO | WO 94/27666 A1 | 12/1994 |
| WO | WO 00/22981 A1 | 4/2000 |
| WO | WO 03/090834 A1 | 11/2003 |
| WO | WO 2005/094935 A1 | 10/2005 |

OTHER PUBLICATIONS

Medtronic Eupalamus Deflectable Stylet, Premarket Notification document, Medtronic, Inc., 8 pgs.; Oct. 18, 2000.

Web site print-out: New Implantation Tool, Steerable Stylet Clinical Assessment Study, Fikru Maru, Joachim Kreutzer, Rolf Pieper, Peter Steen Hansen, Peter Zwicky, Mariette Schonbeck, Thomas Vesterlund, HeartWeb Organization, vol. 4, No. 1, Article No. 98110008, 8 pgs.; Nov. 1998.

Christopher M. Putman and John C. Chaloupka, "Use of Large-Caliber Coronary Guiding Catheters for Neurointerventional Applications," Interventional Neuroradiology Service, Dept. of Radiology, Yale University School of Medicine (New Haven, CT), (Aug. 23, 1995).

William Leventon, "Medical Tubing Offers More (and Less) to Device Makers Modern tubing boasts more properties with less bulk than ever before. But the Improvements will cost you.," Magazine, Medical Device & Diagnostic Industry, (Jan. 1, 2002).

William Leventon, "Extrusion Changes to Meet New Challenges Tub makers report on developments in materials, processes, and the extrusion business.," Magazine, Medical Device & Diagnostic Industry, (Nov. 8, 2003).

* cited by examiner

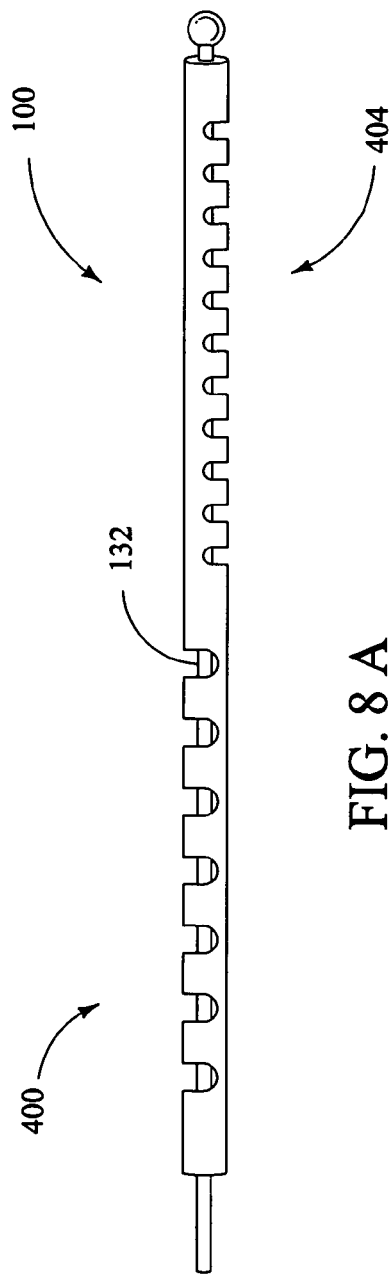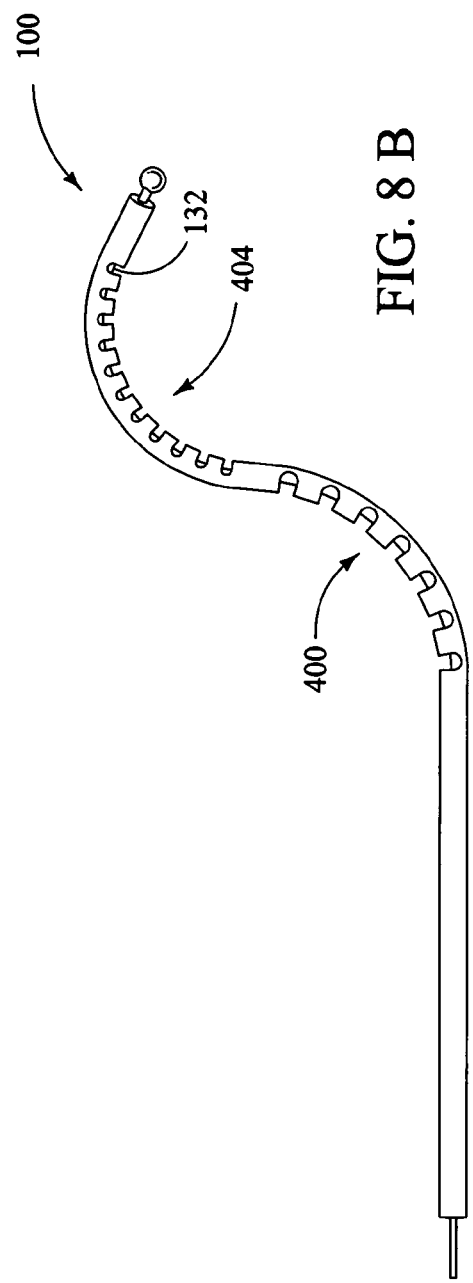

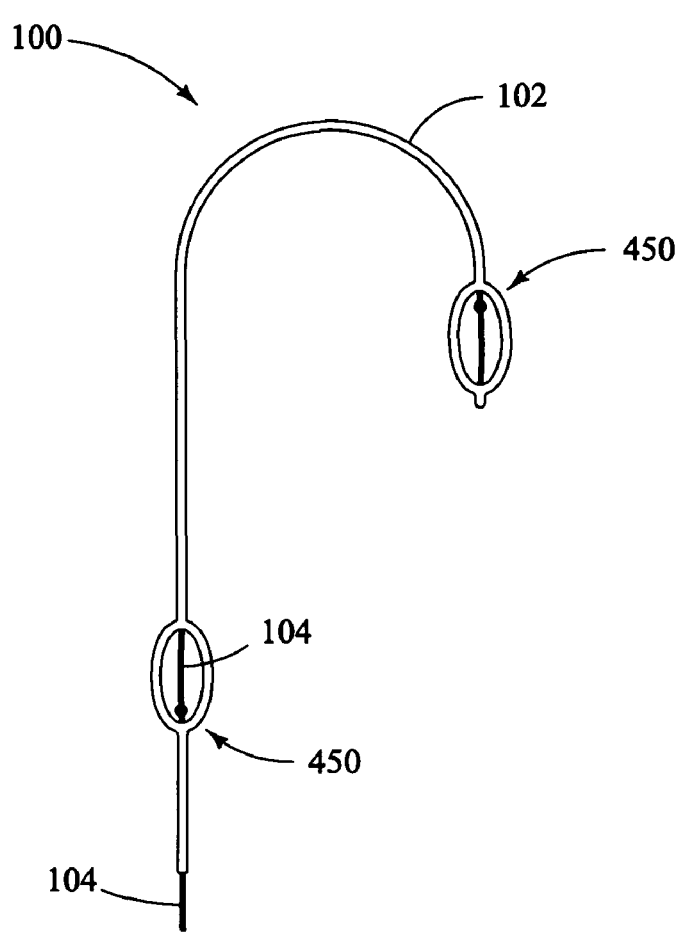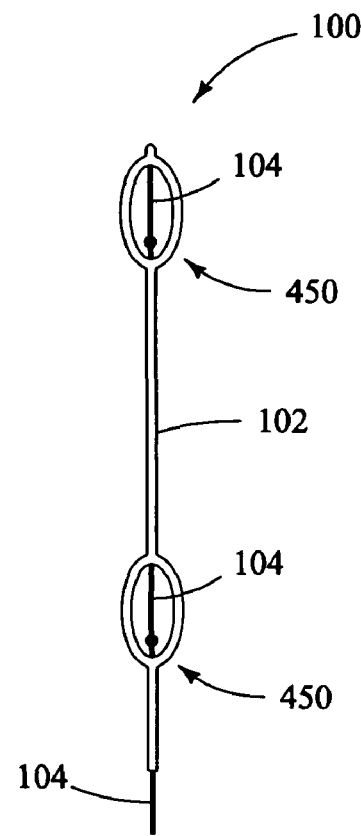
FIG. 13 A
FIG. 13 B
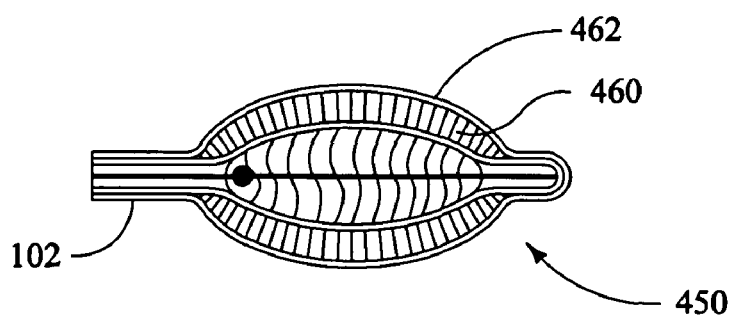
FIG. 13 C

HANDLE AND ARTICULATOR SYSTEM AND METHOD

TECHNICAL FIELD

The invention relates to a system and method for navigating a medical device through a tortuous pathway, such as a vascular system.

BACKGROUND OF THE INVENTION

Stylets are commonly navigated through tortuous pathways, such as the vascular system of a body. In some procedures, a catheter is carried by the stylet. Once in the desired location, the stylet is retracted to leave the catheter in place. In the event that the desired location of the catheter changes, or an additional medical device is desired to be placed within the catheter, the stylet must be reintroduced into the catheter and rerouted through the tortuous pathway. Such rerouting causes delay during medical procedures and has the potential to cause damage to the cells and tissues making up the tortuous pathway.

Further, several methods have been provided to navigate the distal end of a stylet through a tortuous pathway. However, these methods have been relatively cumbersome and unintuitive. For example, many of the methods require the use of two hands to properly navigate, or require a user to move digits in an awkward fashion. Such methods increase the risk of medical procedures by increasing the time required to perform the procedure and increasing the number of failed attempts to navigate certain pathways. Such methods can also fatigue the hand of the medical practitioner.

SUMMARY OF THE INVENTION

The invention provides an assembly that includes an articulator comprising proximal and distal end portions, and a corresponding handle, the articulator and handle being adapted to be mated at the proximal end portion, in order to permit the resulting assembly to be operated in an ergonomically improved manner. Preferably, the handle can be releasably mated with the articulator, and the ergonomically improved manner comprises single-handed operation. In a further preferred embodiment, the distal end of the articulator can be controlled so as to form a plurality of desired shapes, depending on the tortuous path, and even more preferably, provides a non-traumatic distal end. By "non-traumatic" as used herein, we refer to a material and/or configuration of the distal end that does not unduly damage cells or tissue along the tortuous path.

The assembly can be used to control the movement of the articulator in a desired manner within a three dimensional coordinate system, including X, Y and Z axes corresponding to the X dimension, linearly (in a proximal-distal direction), the Y dimension, radially, emanating from the core of the articulator, and the Z dimension, in a generally concentric dimension, as by rotating around the central axis of the articulator.

In turn, the handle and articulator assembly can be operated to provide a controlled array of distal end portion forms that include, but are not limited to the following forms and combinations thereof: straight, bends (e.g., simple or compound), curves (e.g., continuous or progressive, multiple curves at desired intervals (e.g., adjacent curves ("S" configurations)), complex curves, repeating curves (e.g., undulations, sine wave), full circle), and twists and turns.

Such shapes can be accomplished in a variety of ways, including by operation of the handle alone, or in combination with articulator regions having varying features, e.g., varying stiffness and/or diameter, different materials, use of notches, and/or by the use of ancillary parts (e.g., membranes, baskets) or coatings, and combinations thereof.

The handle of this invention is particularly well suited for articulators that operate on a "push-pull" basis that involves the use of relative motion as between a plurality of parts, e.g., a core wire and an adjacent or surrounding outer wire.

The handle is preferably provided with an ergonomic design that allows it to be intuitively manipulated in a single-handed fashion, in order to navigate an articulator through a tortuous pathway. In some embodiments, the handle is adapted to articulate the distal end of the articulator when it is squeezed, such as between one or more fingers and the thumb or palm of a hand. The handle can also be biased to articulate the articulator to a predetermined position when it is not being squeezed. Such a handle provides an intuitive and accurate way to navigate the articulator through a tortuous pathway.

In some preferred embodiments, the operation of a handle can be analogized to the "cricket clickers" made famous in the parachute drops of World War II. When pinched between the thumb and one or more opposing fingers, rather than making the famous clicking sound, the handle instead operates to move a corresponding plurality of parts relative to each other in a linear direction, such that the articulator itself is progressed and manipulated in a desired fashion. Simultaneously, the operating hand can itself be manipulated, e.g., turned and/or progressed toward or from the region of the distal end, in order to provide movement along one or more other axes or directions.

Single handed operation includes, but is not limited to, finger operable, such as by a plurality of fingers such as the thumb and forefinger to articulate the distal end of an articulator and/or turning a hand to turn the apparatus in its entirety (e.g., about an axis). In some embodiments, a one to one torqueability ratio is provided between the hand and the distal end of the articulator, so that turning the hand one complete revolution corresponds to turning the distal end of the articulator one complete revolution. In addition, advancing a hand can move the entire apparatus in a distal-proximal direction. One or more of these types of movements, coupled with features of the articulator itself (materials, structure, etc), permit accurate, real time movement of the distal portion, with minimal trauma.

In turn, the invention provides a method and apparatus for improved navigation of medical devices through tortuous pathways. Some embodiments of the invention allow for the means to articulate a distal end of an articulator from outside a patient. In addition, preferred embodiments of the apparatus are compatible with a variety of diagnostic and therapeutic interventional devices. Such embodiments of the invention are useful in many medical areas, such as interventional cardiology (e.g., stents and catheters), peripheral vascular intervention (e.g., iliac, femoral-popliteal, renals, and carotids), cardiac rhythm management (e.g., leads), neuro interventional (e.g., balloon remolding of aneurysms, arteriovenous malformation, tumor embolizations, vasospasms, clot retrieval), and urinary applications (e.g., the placement of stents and retrieval of stones).

In some embodiments, the invention provides a handle that can be used to navigate an articulator through tortuous pathways, such as through a human vascular system. The handle can be adapted to allow the articulator to be quickly and easily detached, such as during a medical procedure. Once detached, other medical devices, such as catheters, can be routed over or through the articulator from either end to gain access to the tortuous pathway. The handle can then be reattached and the articulator repositioned within the tortuous pathway. Such a reattachable handle allows for greater flexibility in selecting medical devices and reduces medical procedure time.

The handle can also have an ergonomic design that allows it to be intuitively manipulated to navigate an articulator through a tortuous pathway. In some embodiments, the handle is adapted to deflect the distal end of the articulator when it is squeezed, such as between one or more fingers and the thumb or palm of a hand. The handle can also be biased to deflect the articulator to a predetermined position when it is not being squeezed. Such a handle provides an intuitive and accurate way to navigate the articulator through a tortuous pathway.

Embodiments of the invention include a handle for manipulating an articulator. The handle includes at least one accessible attachment mechanism useful for reattachably attaching the articulator and the handle during a medical procedure. In some embodiments of the invention, the handle is adapted to deflect a distal portion of the articulator when squeezed. Embodiments of the invention also include methods of making and using such a handle.

BRIEF DESCRIPTION OF THE DRAWING

In the Drawing:

FIG. 4B shows a side plan view of a handle and locking mechanism in accordance with embodiments of the invention.

FIG. 6A shows a perspective view of an articulator disposed within a vessel in accordance with embodiments of the invention;

FIG. 8A provides a side plan view of an articulator in accordance with embodiments of the invention;

FIG. 8B provides a side plan view of an articulator in a curved shape in accordance with embodiments of the invention;

FIG. 13A provides a side plan view of an articulator in a curved shape in accordance with embodiments of the invention;

FIG. 13B provides a side plan view of an articulator in accordance with embodiments of the invention;

FIG. 13C provides a side plan view of an enlarged portion in accordance with embodiments of the invention;

DETAILED DESCRIPTION OF THE INVENTION

An assembly in accordance with some embodiments of the present invention includes a handle useful for articulating an articulator into and within various tortuous pathways (e.g., body lumens) to facilitate the performance of various minimally invasive medical procedures. Examples of body lumens include blood vessels, tear ducts, lymph vessels, lumens for the passage of bile, lumens for the passage of urine, and gastrointestinal lumens. Examples of minimally invasive medical procedures include percutaneous transluminal coronary angioplasty (PCTA), endoscopic retrograde cholangio-pancreaticography (ERCP), endovascular treatment of brain aneurysms, atherectomy procedures, biopsy procedures, stenting procedures, and diagnostic procedures (e.g., angiograms).

A handle of the present invention can be used to position and/or deliver a variety of medical devices. The medical device used in conjunction with the handle and articulator can be positioned in any suitable manner with respect to the articulator, including within, surrounding, along the length of, or axially concentric with the articulator (e.g., within or surrounding the articulator itself), axially adjacent the articulator, or positioned in one or more predetermined positions along the length of the articulator (e.g., distally or along its length). Examples of medical devices that can be used in conjunction with a handle and an articulator in accordance with the present invention include catheters, leads, stents, biopsy tools and angiographic die injection catheters.

The handle can be used to articulate the articulator (e.g., control or adjust various characteristics of the articulator, including its course and shape, its stiffness, and/or its length), in order to facilitate its navigation, and in turn the placement or positioning of associated medical devices, such as internal or external catheters and/or devices adapted to be positioned or deployed along the length of the articulator in the course of its use.

The following detailed description should be read with reference to the figures, in which like elements in different drawings are numbered identically. The figures, which are not necessarily to scale, depict selected embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
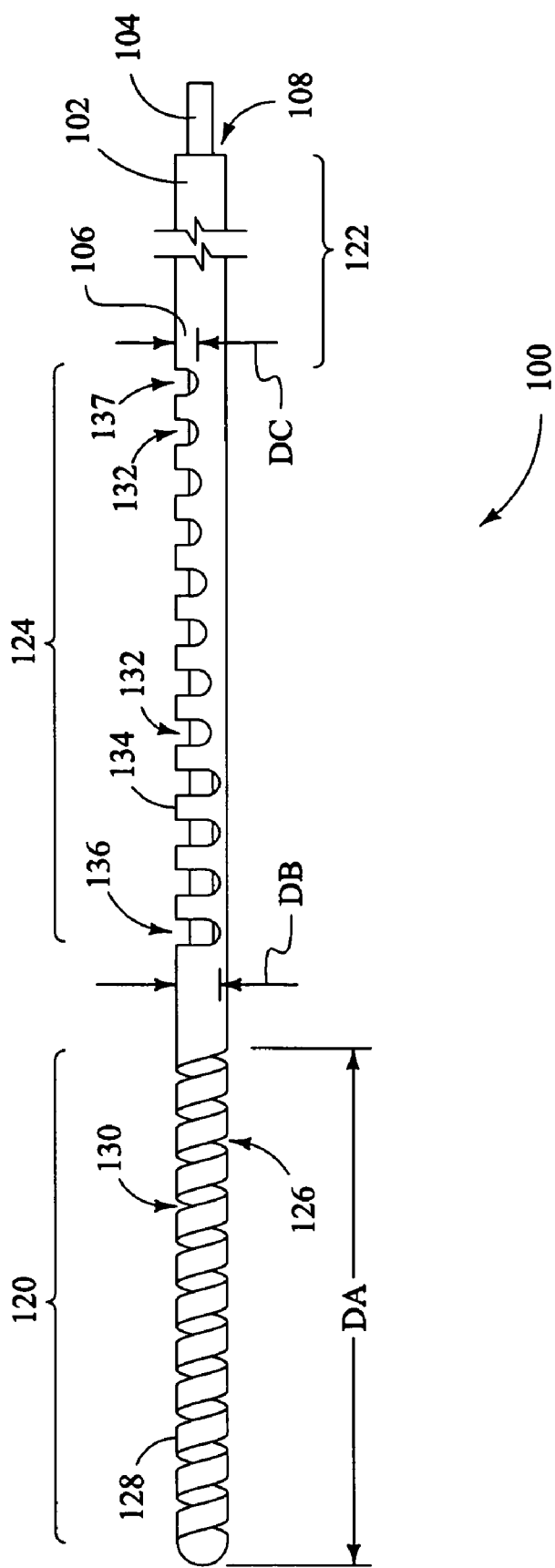
FIG. 1 provides a side plan view of an articulator in accordance with embodiments of the invention.

FIG. 1 is a side view of an articulator 100 that can be articulated by a handle in accordance with some embodiments of the invention. The articulator 100 can comprise a first wire 102 and a second wire 104. First wire 102 comprises a wall 106 defining a lumen 108. In the embodiment of FIG. 1, a portion of second wire 104 is disposed within lumen 108 defined by first wire 102. The articulator can be articulated by applying a relative force differential between the first wire and the second wire sufficient to move the first wire relative to the second wire. Also, in the embodiment of FIG. 1, first wire 102 comprises a distal portion 120, a proximal portion 122, and an intermediate portion 124. In the embodiment of FIG. 1, proximal portion 122 of first wire 102 comprises a solid portion of wall 106.

In the embodiment of FIG. 1, distal portion 120 of first wire 102 comprises a portion of wall 106 that defines a cut 126. In FIG. 1, cut 126 is shown having a generally helical shape. With reference to FIG. 1, it will be appreciated that cut 126 defines a plurality of turns 128. In the embodiment of FIG. 1, turns 128 are disposed with spaces 130 disposed between adjacent turns 128. A dimension DA of distal portion 120 of articulator 100 is illustrated using dimension lines in FIG. 1.

In some embodiments of the present invention the distal portion 120 of articulator 100 is capable of assuming shapes having various lengths. In some useful methods in accordance with the present invention, the dimension DA of distal portion 120 of articulator 100 can be varied by urging relative motion between first wire 102 and second wire 104. Also in some useful methods in accordance with the present invention, a lateral stiffness of distal portion 120 of articulator 100 can be varied by urging relative motion between first wire 102 and second wire 104.

In the embodiment of FIG. 1, intermediate portion 124 of first wire 102 is adapted to assume one or more generally curved shapes. In the embodiments shown, first wire 102 comprises a portion of wall 106 that defines a plurality of slots 132. A rib 134 of intermediate portion 124 of first wire 102 is defined by each adjacent pair of slots 132. Slots 132 can be positioned and dimensioned such that intermediate portion 124 of first wire 102 can be urged to selectively assume various generally curved shapes. A dimension DB of a most-distally located slot 136 is shown with dimension lines in FIG. 1. In the exemplary embodiment of FIG. 1, dimension DB is equal to about the outer diameter of first wire 102 minus the thickness of wall 106. A dimension DC of a most-proximally located slot 137 is also shown with dimension lines in FIG. 1. In the exemplary embodiment of FIG. 1, dimension DC is less than about one half the outer diameter of first wire 102. Of course, the distal portion 120 of the articulator 100 could also be adapted to assume one or more generally curved shapes. For the sake of simplicity, the discussion below will only refer to the articulation of the distal end or portion, although it will be understood that the distal and/or intermediate portions of the articulator can be adapted to assume one or more generally curved shapes, lengths and/or stiffnesses.

Figure 2:
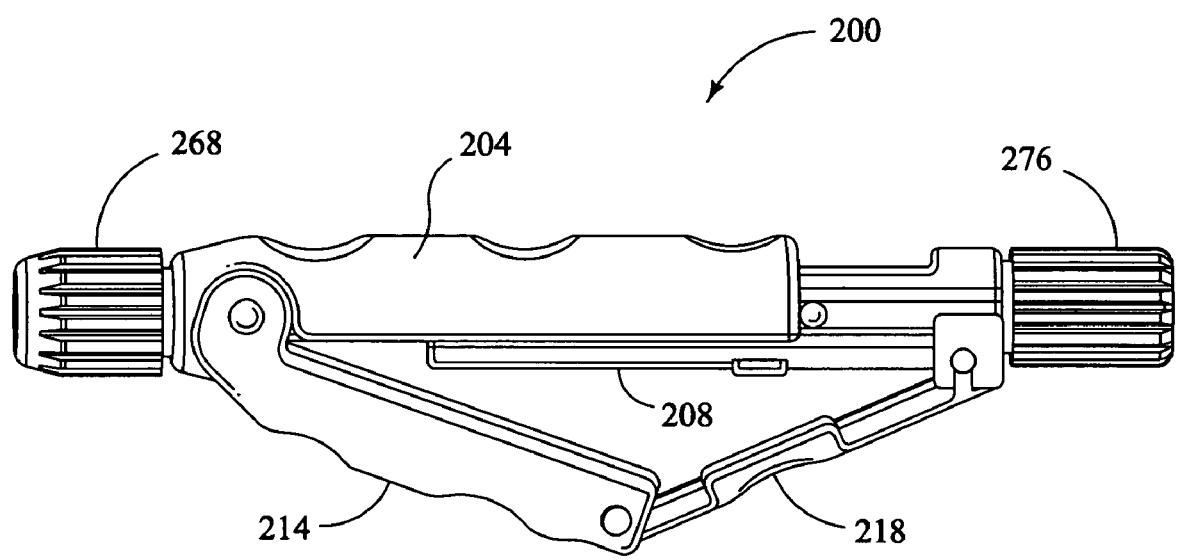
FIG. 2 shows a side plan view of a handle in accordance with embodiments of the invention.
Figure 3:
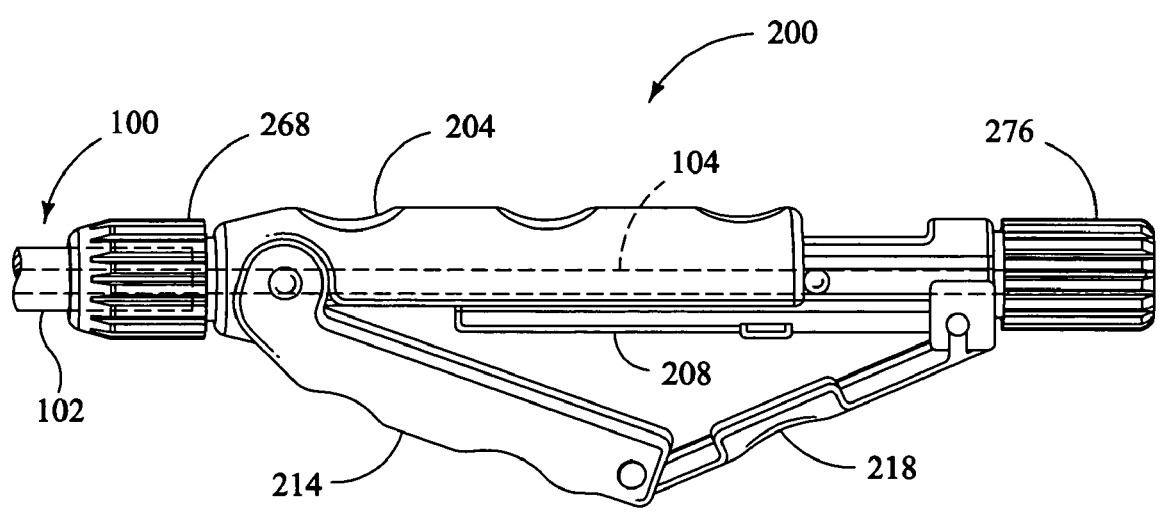
FIG. 3 shows a side plan with partial hidden line view of a handle and an articulator in accordance with embodiments of the invention.
Figure 4:
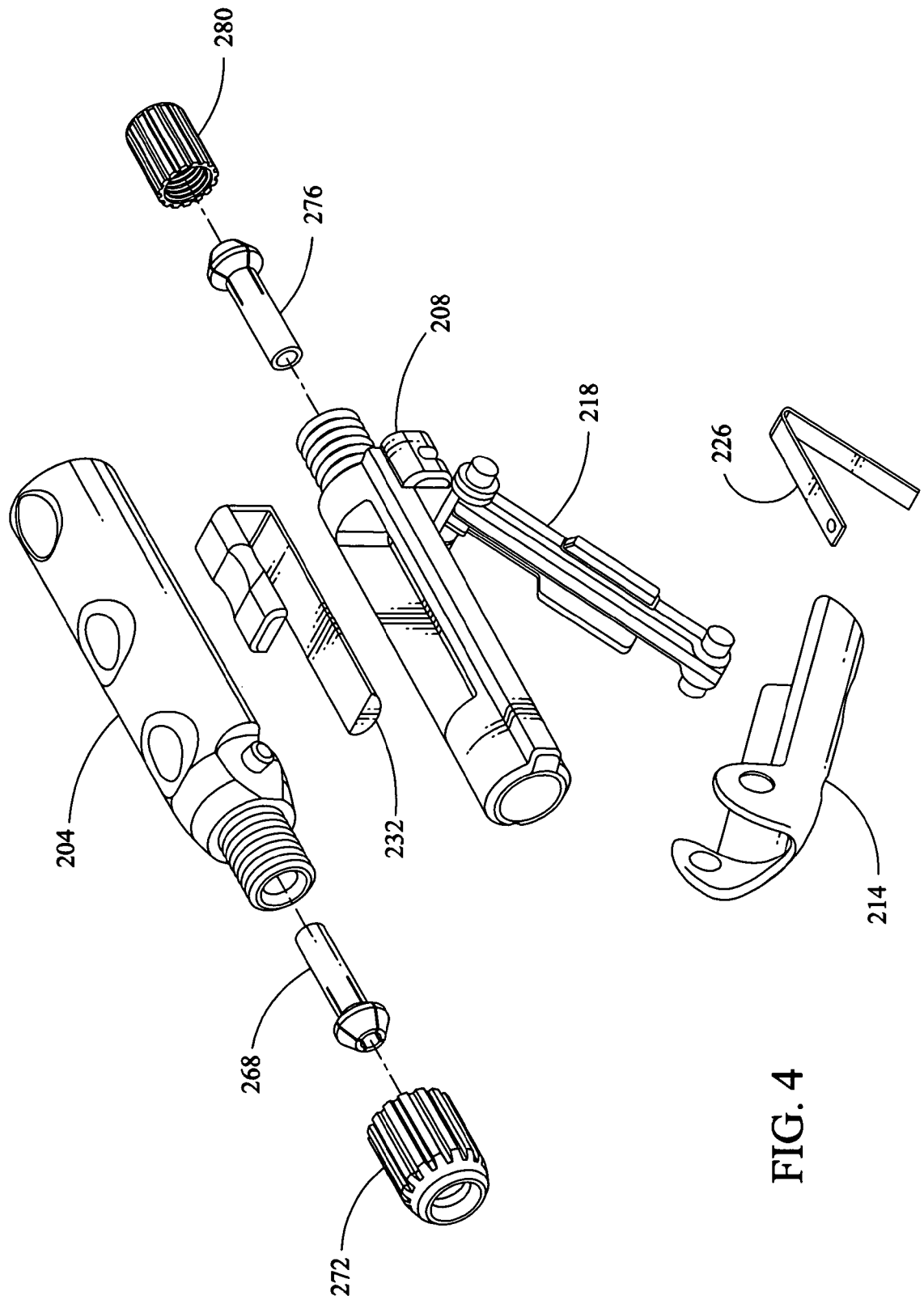
FIG. 4 shows an exploded view of a handle in accordance with embodiments of the invention.

As shown in FIGS. 2-4, some embodiments the invention include a handle 200 useful for articulating the articulator 100. As discussed above, first wire and the second wire can be moved relative to each other by applying a longitudinal force differential between them, thereby allowing the distal end of the articulator 100 to be effectively articulated from the proximal end to navigate tortuous pathways. In some embodiments, a handle 200 can be provided to move the first wire relative to the second wire by applying a longitudinal force differential between the first wire and the second wire. For example, the handle 200 can comprise a first portion 204 and a second portion 208, the first portion 204 being functionally coupled to a proximal portion of the first wire and the second portion 208 being functionally coupled to a proximal portion of the second wire. In such embodiments, the first and second portions can be moved relative to each other (e.g., slidingly) to move the first and second wires relative to each other to articulate the distal end of the articulator 100.

The handle 200 can be used to articulate the distal end of an articulator 100 by any suitable manner. In some embodiments, a user can articulate the distal end of an articulator 100 by squeezing the handle 200. For example, the handle 200 can have a first actuating member 214 pivotably coupled to the first portion 204 and a second actuating member 218 pivotably coupled to the second portion 208. The first and second actuating members can also be pivotably coupled to each other. In such embodiments, squeezing the first and/or second actuating members relative the first and/or second portions cause the first and second portions to move longitudinally relative to each other, thereby causing a longitudinal force differential between the first and second wires and a resulting articulation in the distal region of the articulator 100. Such embodiments are useful for allowing the articulator 100 to be manipulated with one hand, via a natural squeezing motion of, for example, the index and/or middle fingers and thumb.

In some embodiments, a first portion 204 adapted to be engaged by one or both of the thumb and the palm of a human hand can be provided. Further, a first actuating member 214 adapted to be engaged by one or both of the index and middle fingers of the human hand can be provided. When a user squeezes the actuating member relative to the first portion 204 the distal end of the articulator 100 can be articulated.

The handle 200 can also be adapted to bias the articulator 100 into a relatively unarticulated position and/or allow the articulator 100 to be locked into an articulated position. For example, as shown in FIG. 4, a biasing member 226 such as a spring can be provided to bias the actuating members to allow the actuator to maintain a relatively unarticulated position. In some embodiments, the handle 200 includes a biasing member 226 to bias a distal end of the articulator 100 to a desired position. For example, the biasing member 226 can be a spring. The handle 200 can bias the distal end of the articulator 100 to a straight position or to a curved position.

In some embodiments, the handle 200 is adapted to lock a distal end of the articulator 100 in a desired position. In some embodiments, as shown in FIG. 4, a locking mechanism 232 can be provided to lock the articulator 100 into a desired articulated position, allowing the operator to cease providing force to the actuating members while maintaining the desired position. Some embodiments of the invention allow a user to lock the distal end of an articulator 100 in a desired position. This is useful, for example, when a user wants to advance or retract the distal end of an articulator 100 within a tortuous pathway while maintaining a generally constant articulation. For example, the handle 200 can be squeezed to an actuated position that locks the pivot members to give the articulator 100 a full bend curve at its distal end. If squeezed again, the pivot members can unlock and resume the neutral position.

Figure 4A:
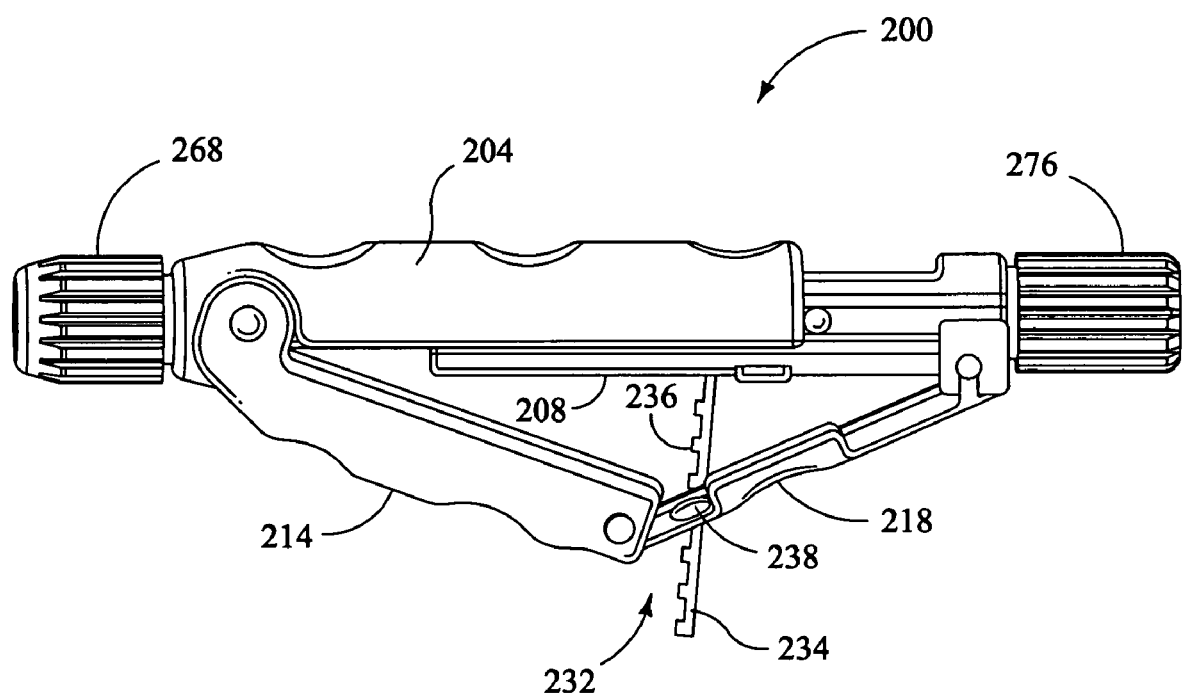
FIG. 4A shows a side plan view of a handle and locking mechanism in accordance with embodiments of the invention.
Figure 4:
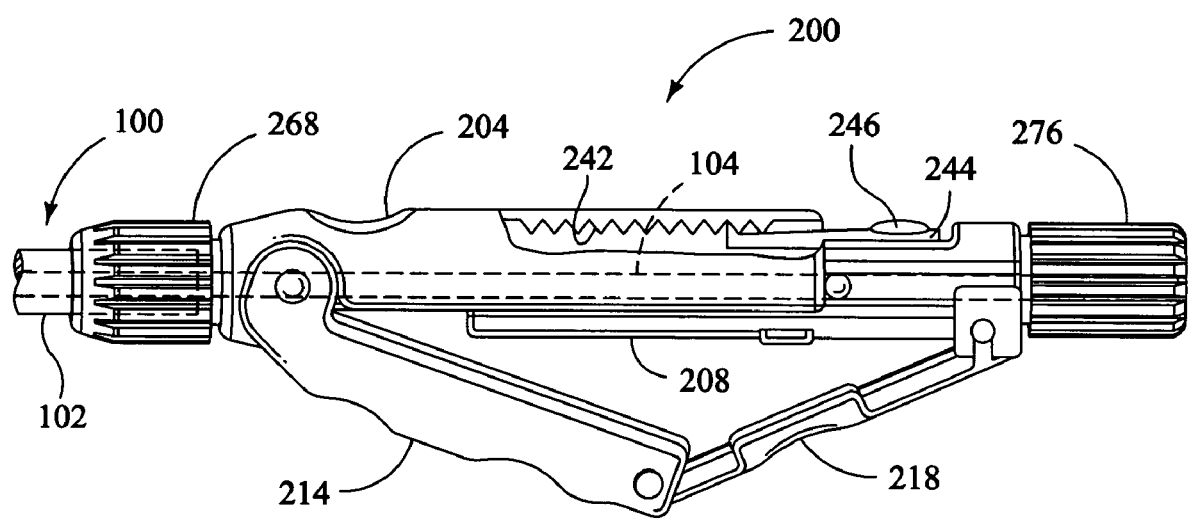

Further, any number of intermediate positions can be provided to lock the distal end in a variety of positions between full articulation and neutral. For example, as shown in FIG. 4A, locking mechanism 232 can comprise an elongated member 234 with one or more teeth 236. The elongated member 234 can extend through an aperture 238 defined in second actuating member 218 and be biased to engage with the side wall of the aperture 238. In use, a user would pull back on elongated member 234 to disengage it from the aperture 238. The actuating members can then be manipulated until the distal end of the articulator 100 is in a desired position. The elongated member 234 can then be released so that it can engage with the aperture 238 to lock the distal end of the articulator 100 in the desired position.

Another embodiment is shown in FIG. 4B. In this embodiment, the handle includes a rack 242 and a paw 244. As shown in FIG. 4B, the paw 244 can engage the rack 242 at a variety of different teeth positions to lock the articulator into a desired position. In some embodiments, a release 246 can be provided that allows the articulator to return to the neutral position when actuated.

Some embodiments of the handle 200 comprise at least one accessible attachment mechanism 260 useful for reattachably attaching the articulator 100 and the handle 200 during a medical procedure. In some embodiments, the accessible placement of the attachment mechanism 260 allows a user to attach and/or detach the articulator 100 from the handle 200 without substantial disassembly of the handle 200, such as during the course of a medical procedure. In some embodiments, the attachment mechanism 260 detachably attaches the articulator 100 to the handle 200, thereby allowing a user to detach and reattach the articulator 100 to the handle 200 a plurality of times. A relatively easy and quick detaching system is useful for allowing an operator to detach the handle 200 from the articulator 100 and later reattach it without compromising steerability. Such detachment can be desirable, for example, to place or remove a catheter from the articulator 100 and reattach the handle 200 to resume navigation.

The first and second wires can be detachably attached to the second and first portions of the handle 200 by any suitable means. For example, the first portion 204 can be detachably attached to the proximal portion of the first wire and the second portion 208 can be detachably attached to the proximal portion of the second wire. In such embodiments, when the first portion 204 and second portion 208 are moved longitudinally relative to each other a longitudinal force differential is created between the first and second wires.

In some embodiments, as best shown in FIG. 4, a first collet 268 and collet nut 272 assembly carried by the first portion 204 is used to detachably attach the first wire and a second collet 276 and collet nut 280 assembly carried by the second portion 208 to detachably attach the second wire. The first and second collet and collet nut assemblies can be located to provide easy access to an operator of the handle 200, allowing the first and second wires to be detached and reattached to the handle 200 a plurality of times. In some embodiments, the handle 200 has a proximal end and a distal end. The first collet 268 and first collet nut 272 can be located proximate the proximal end and the second collet 276 and second collet nut 280 can be located proximate the distal end to provide easy access for detaching and reattaching the articulator 100 and the handle 200.

Figure 5:
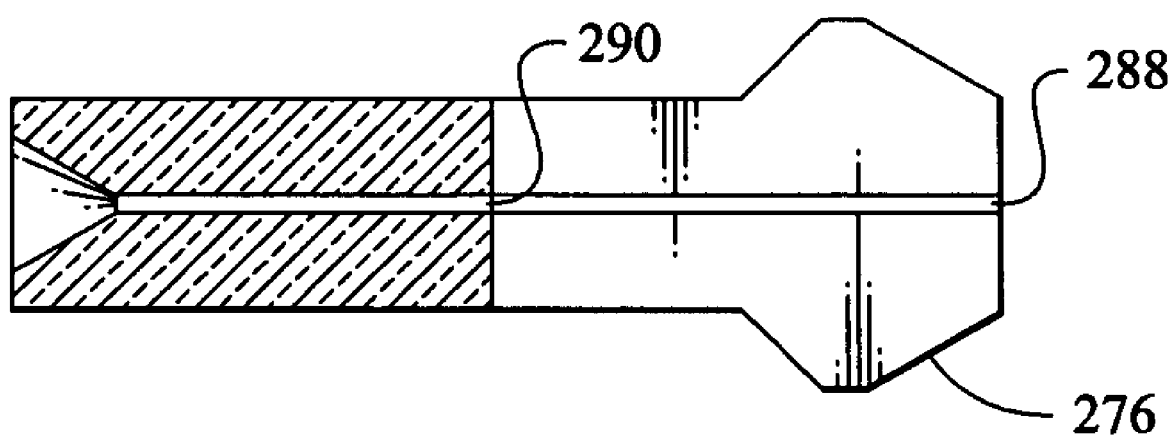
FIG. 5 shows a side plan view of a collet in accordance with embodiments of the invention.

The attachment mechanisms can be adapted to reduce the risk of a user coming into contact with the proximate end of second wire 104. In some embodiments, second collet 276 is adapted to restrict the proximate end of second wire 104 from extending beyond it. For example, as shown in FIG. 5, second collet can define a second collet aperture 288 to receive the second wire 104 and a collet stop 290 can be provided to retain the second wire 104. The collet stop 290 can be located at a position to enable the second wire 104 to be retained within in the collet a desirable amount. Further, second collet nut 280 can be provided with a second collet nut stop 296 to restrict the second wire 104 from extending beyond the proximal end of the handle 200.

Any of the various handle 200 and articulator assemblies described above can be adapted to further improve its functionality during the course of a medical procedure. For example, the assembly can have a one-to-one torqueability ratio between the handle 200 and the distal end of the articulator 100. In such embodiments, when the user rotates the handle 200 a complete turn, the distal end of the articulator 100 is also rotated a generally complete turn. Such a system provide for more precise and reproducible navigability.

Further, in some embodiments the handle 200 is relatively light. For example, the handle 200 can be light enough that in the event it is dropped during a medical procedure, its weight does not kink the articulator or pull the articulator out of a patient. In some embodiments, the handle weighs about 5 grams to about 15 grams. In other embodiments, the handle weighs about 5 grams to about 10 grams. In yet other embodiments, the handle weighs about 6 grams to about 8 grams.

The various components of the handle 200 can comprise any suitable material. In some embodiments, the pivot members and first and second portions can comprise a plastic. Such embodiments are useful for providing the relatively light handles described above. In some embodiments, the various components of the handle comprise a metal. Such embodiments are useful for allowing the handle 200 to be sterilized by heat between procedures (e.g., by autoclave). Such a reusable handle 200 can be packed with articulator 100 groups that target specific operations to offer a range of lengths diameters and function which allow the user flexibility in articulator selection.

The invention also include methods of using any of the handles and articulators described above. In some embodiments, the method comprising the steps of performing a first step of a medical procedure by navigating a distal end of an articulator 100 through a tortuous pathway. Once a desired location has been reached, articulator 100 and the handle 200 can be detached. A second step of a medical procedure can be performed, such as sliding a second medical device (e.g., catheter) over the articulator 100 and into the tortuous pathway. The handle 200 and the articulator 100 can then be reattached and the articulator navigated into another desired location.

As discussed above, such a handle 200 can be useful for articulating an articulator 100. The articulator 100 can comprise any member able to navigate through a tortuous pathway. Such an articulator 100 can have a neutral position when not being actuated by the handle 200. The neutral position can be generally straight, or it can include a bend. Upon activation, the articulator 100 can comprise a progressively larger curve position. At full activation, the distal end of the articulator 100 can have a full curved position.

Articulators in accordance with embodiments of the invention can be of any desirable diameter, length and distal end bend radius consistent with the application in which it will be used. In some embodiments, the articulator can have a diameter of about 0.01 inches to about 0.25 inches (about 0.25 centimeters (cm) to about 1.4 cm), a length of about 10 inches to about 120 inches (about 25 cm to about 305 cm), and the bend of the distal end can have a radius from about 0.0625 inches to about 4 inches (about 0.16 cm to about 10 cm), depending on the desired application.

Articulators can also include, for example, stylets as described by the assignee of the present application in U.S. Pat. No. 6,776,765, the contents if which are hereby incorporated by reference. The stylet assembly has a distal end portion and a proximal end portion and includes a stylet wire having a lumen and a core wire positioned within the lumen with the distal end portion secured to the stylet wire proximate the distal end portion of the stylet wire. The handle 200 includes a hand-held housing structure connected to one of the proximal end portion of the stylet wire or the core wire. In one embodiment, an adjustable tensioner is connected to the other of the proximal end portion of the stylet wire or the core wire to adjust a relative tension force applied between the stylet wire and the core wire. A tension limiter is arranged to limit the tension force to a limit force that is less than a breaking stress force of the stylet wire when the stylet wire is positioned within the lumen of the intravascular device.

Another example of an articulator 100 that can be articulated with handles in accordance with some embodiments of the invention include an adjustable stylet that includes a core wire having a portion surrounded by a compression member preferably comprised of a flat wire spring, as described by the assignee of the present application in U.S. Pat. No. 6,755,794, the contents of which are hereby incorporated by reference. Depending upon the configuration, compression or relaxation of the compression member in response to forces at the tip or handle 200 of the stylet results in adjustments to the characteristics of the stylet, including its stiffness and/or length.

Handles in accordance with some embodiments of the invention can also be used to articulate articulators as described in U.S. patent application Ser. No. 10/973,317, filed Oct. 26, 2004, the contents of which are hereby incorporated by reference. Various characteristics of the articulator 100 can be controlled and adjusted, including its course and shape, its stiffness, and/or its length, in order to facilitate its placement, and in turn the placement or positioning of associated components, such as internal or external catheters and/or devices adapted to be positioned or deployed along the length of the articulator 100 in the course of its use.

In some embodiments, the articulator can be independently curved and stiffened by providing a dual squeeze handle (e.g., two handles as described above in series). In such embodiments, a third wire functionally coupled to the first wire can be provided within a lumen defined by the second wire. The proximal portion of the second wire can be coupled to the proximal portion of the first handle in the series in the manner described herein. The proximal portion of the third wire can be coupled to the proximal portion of the second handle in the series. In such embodiments, curvature or stiffness can be selectively adjusted by actuating either the first or second handle in the series.

Figure 6:
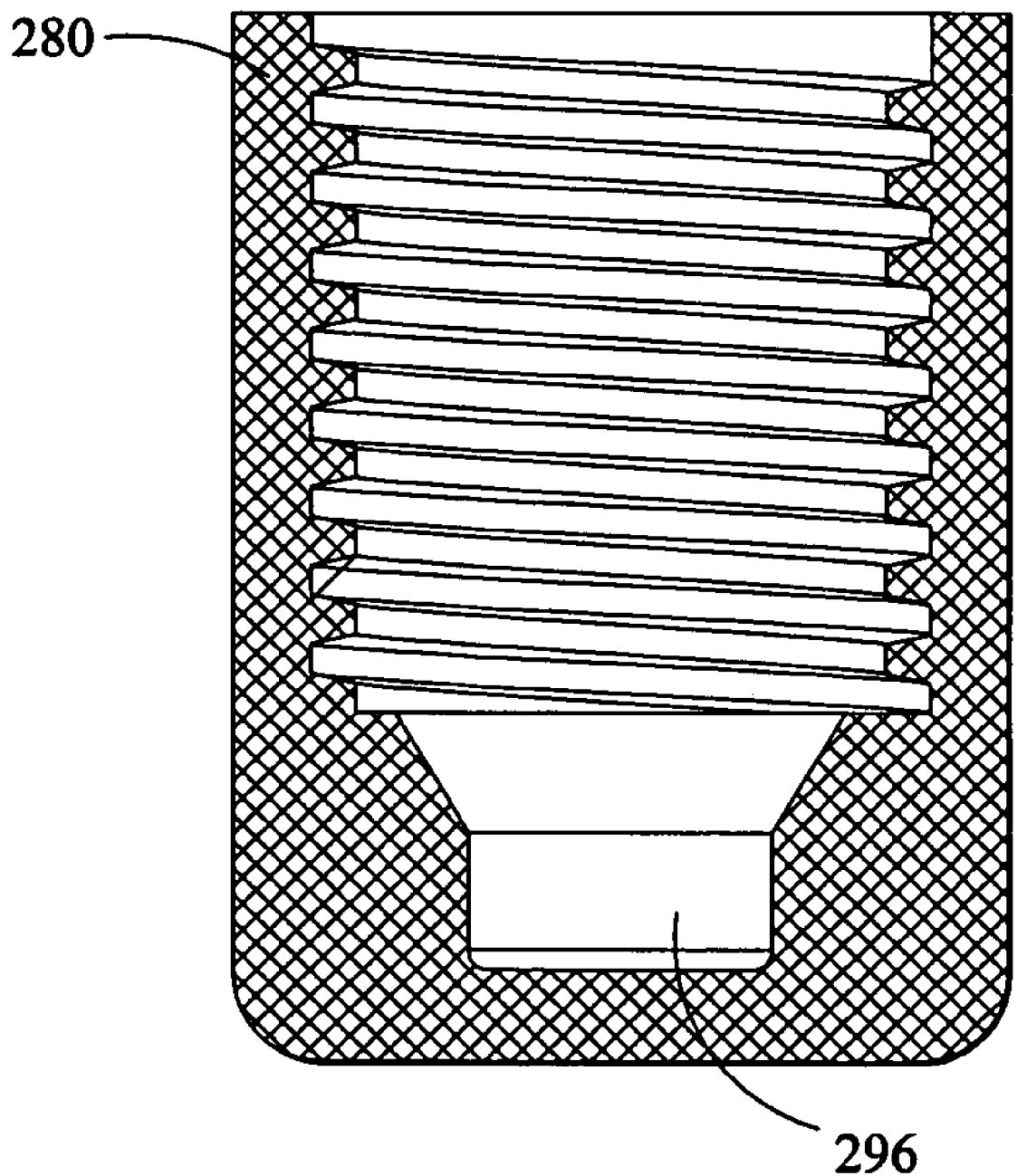
FIG. 6 shows a top plan cut away view of a collet nut in accordance with embodiments of the invention.
Figure 6:
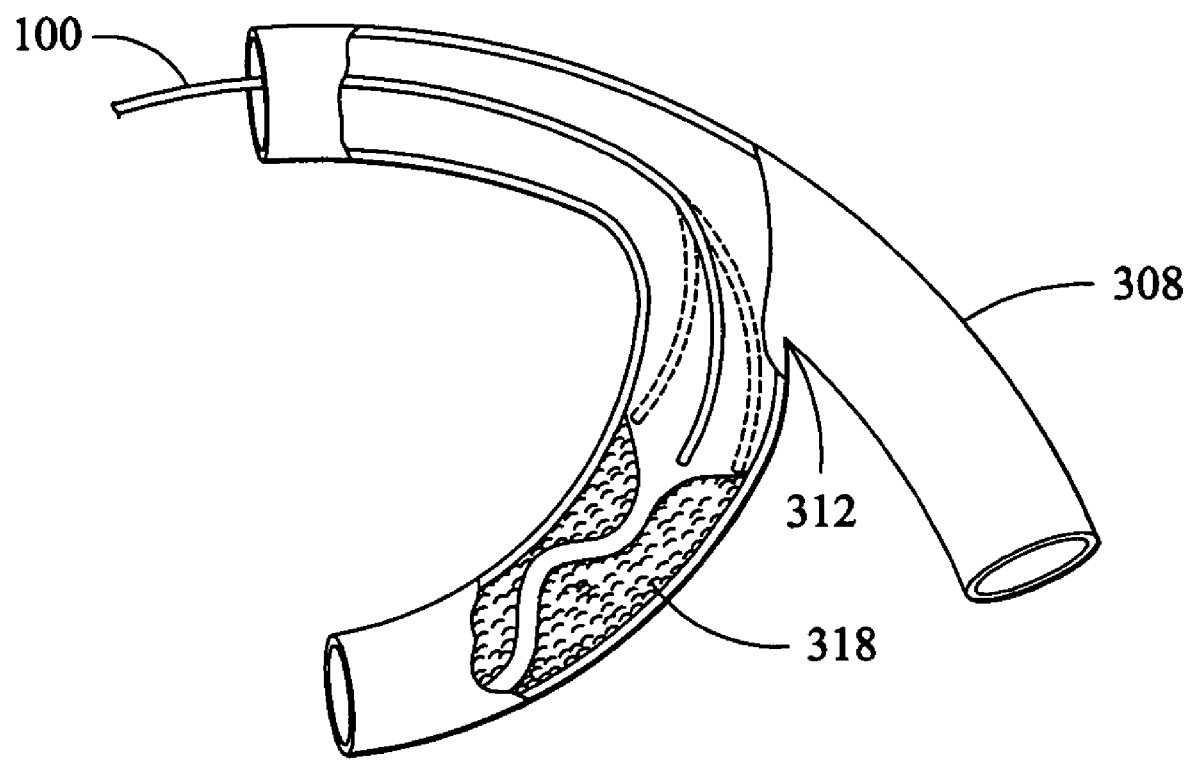
Figure 7A:
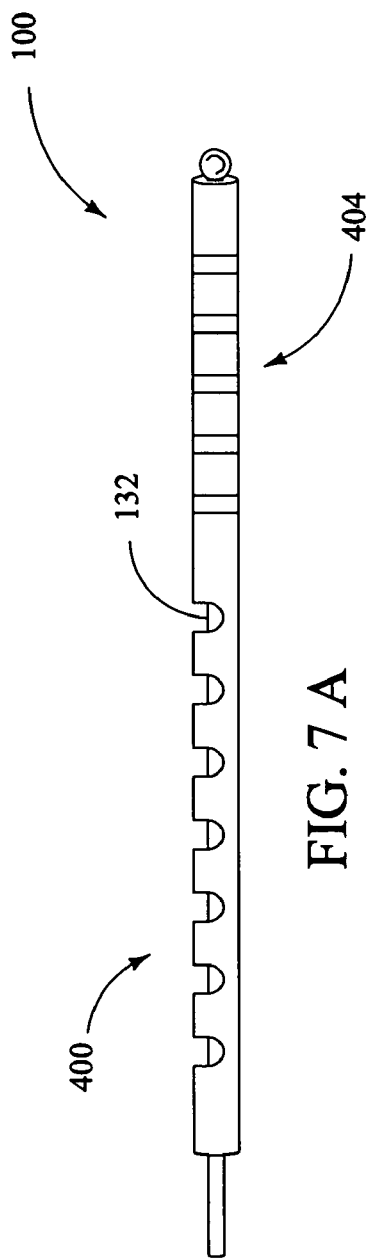
FIG. 7A provides a side plan view of an articulator in accordance with embodiments of the invention.
Figure 7C:
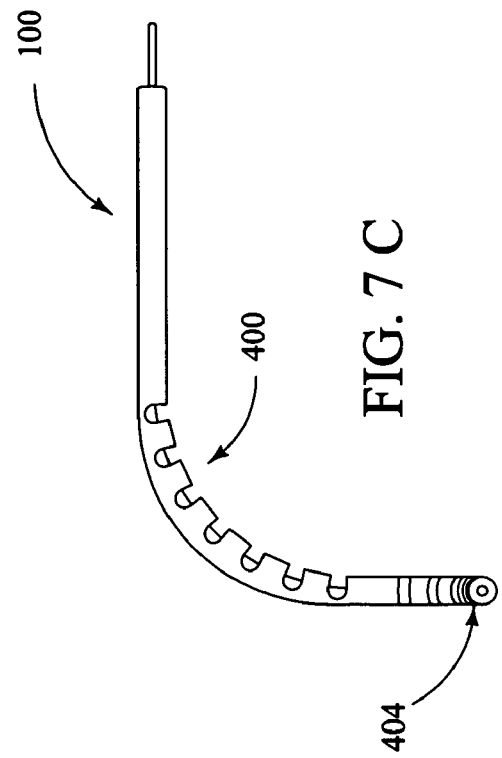
FIG. 7C provides a side plan view of an articulator in a curved shape in accordance with embodiments of the invention.
Figure 7B:
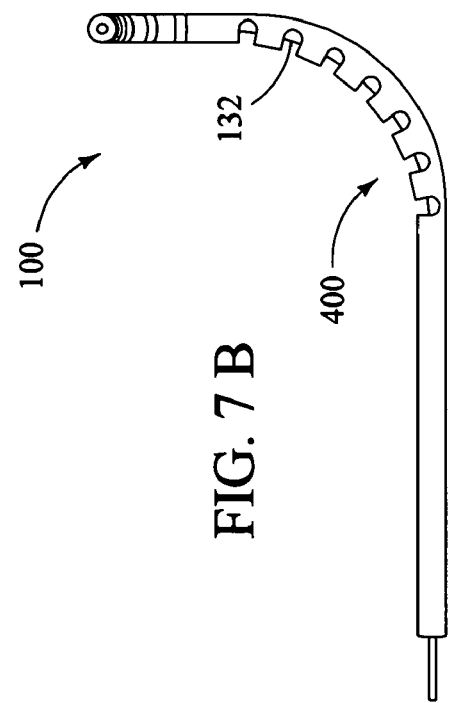
FIG. 7B provides a side plan view of an articulator in a curved shape in accordance with embodiments of the invention.

Articulators 100 as described herein are useful for navigating tortuous pathways, such as the vessel 308 depicted in FIG. 6A. As shown in FIG. 6A, the articulator 100 can be navigated to follow a desired branch of vessel 308 containing a bifurcation 312. Further, also as shown in FIG. 6A, the articulator can be navigated though a tortuous opening within an occlusion 318.

In some embodiments, features such as slots 132 can be provided in the first wire to cause the articulator 100 to curve in a desired direction when a force is applied between the first wire and the second wire. Generally, the location of the curve depends on where the slots are provided, and the radius of the curve depends on the number of slots, the depth of the slots, and how close the slots are to each other. Accordingly, the location and radius of the curve desired for a particular application can be obtained by adjusting these parameters.

Multiple curves can also be provided within the same articulator 100. For example, the distal end of an articulator 100 can be provided with at least two series of features, such as a first slot series 400 and a second slot series 404 as shown in FIGS. 7A-C and 8A-B. The first slot series 400 can have a different orientation about the circumference of the articulator 100 than the second slot series. In the example shown in FIGS. 7A-C, first slot series 400 can be offset from second slot series 404 by about 90 degrees. In such embodiments, when the second wire is pulled relative to the first wire, the articulator will create a first curve in a first direction and a second curve in a second direction. In other embodiments, as shown in FIGS. 8A-B, first and second series of slots can be offset from each other by about 180 degrees. In such embodiments, a generally S-shaped curve is created with the second wire is moved relative to the first wire.

Figure 9:
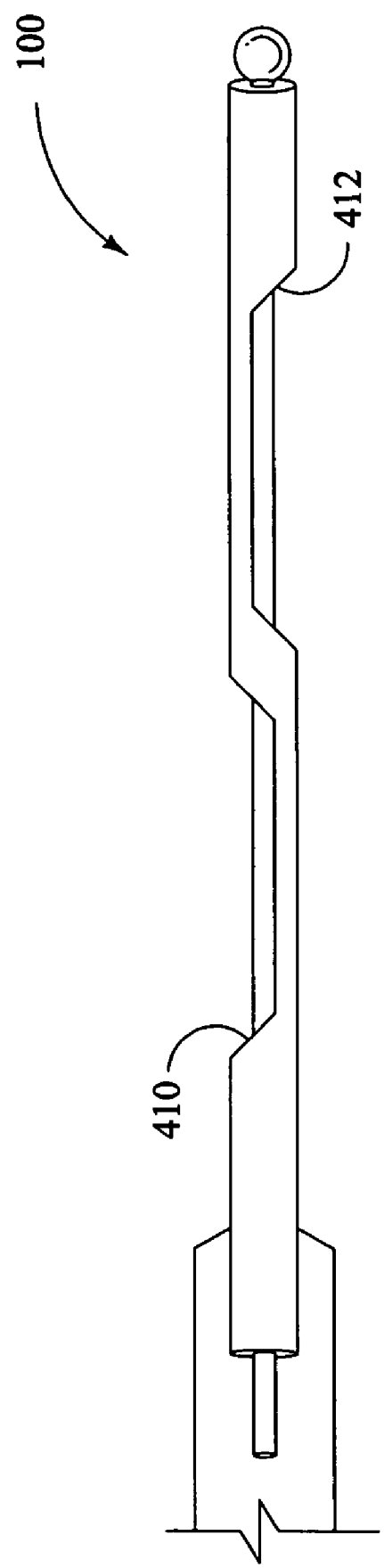
FIG. 9 provides a side plan view of an articulator in accordance with embodiments of the invention.

Another example of features useful to provide compound curves and complex shapes is shown in FIG. 9. In FIG. 9, the first wire comprises at least two resected portions, such as first resected portion 410 and second resected portion 412 each having a length along the longitudinal axis of the articulator 100 (e.g., about 1 inch). Each resected portion can be covered with a flexible coating as described herein. First resected portion 410 can be offset by about 180 degrees from second resected portion 412, thereby creating an S-shaped curve when the second wire is moved relative to the first wire.

Figure 10:
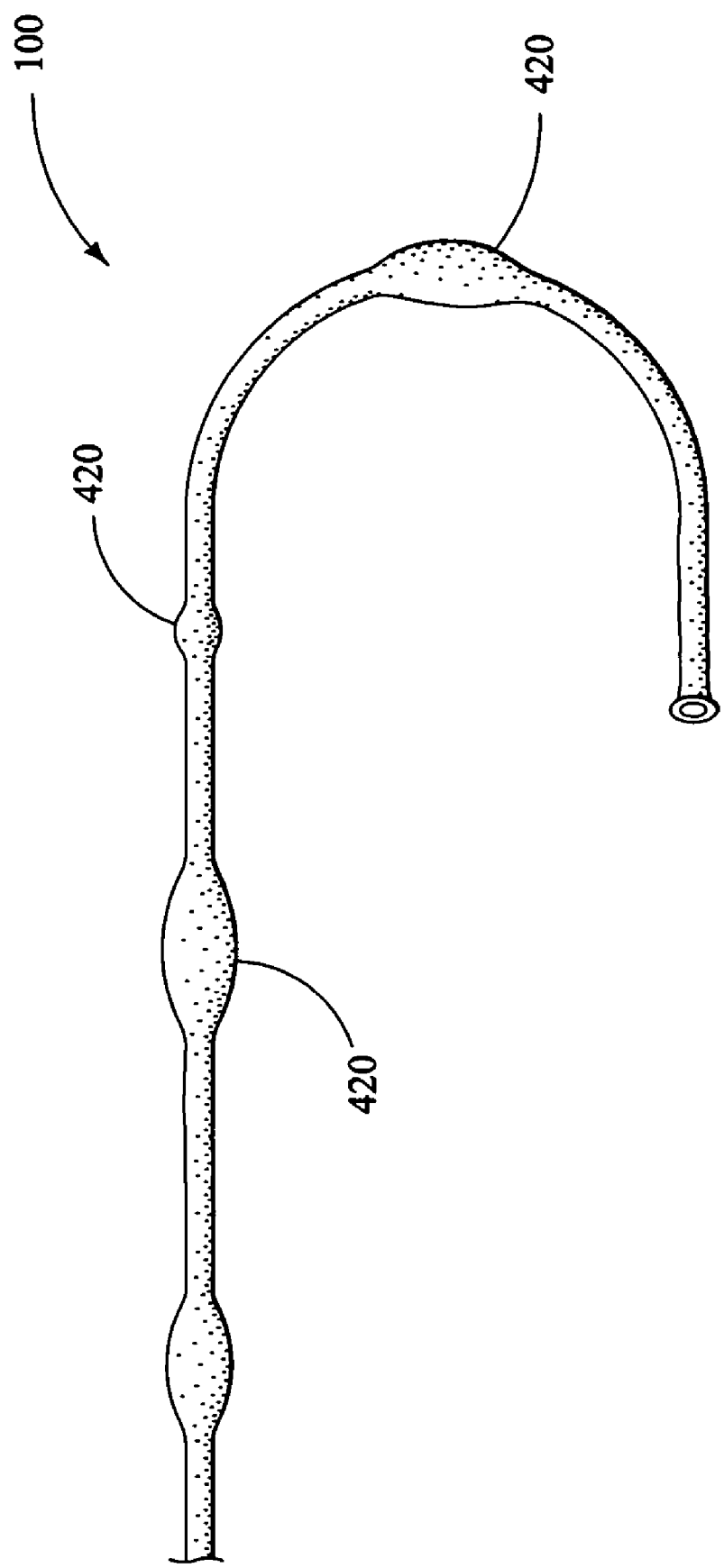
FIG. 10A provides a side plan view of an articulator in a curved shape in accordance with embodiments of the invention.
FIG. 10B provides a side plan view of an articulator in accordance with embodiments of the invention.
Figure 10:
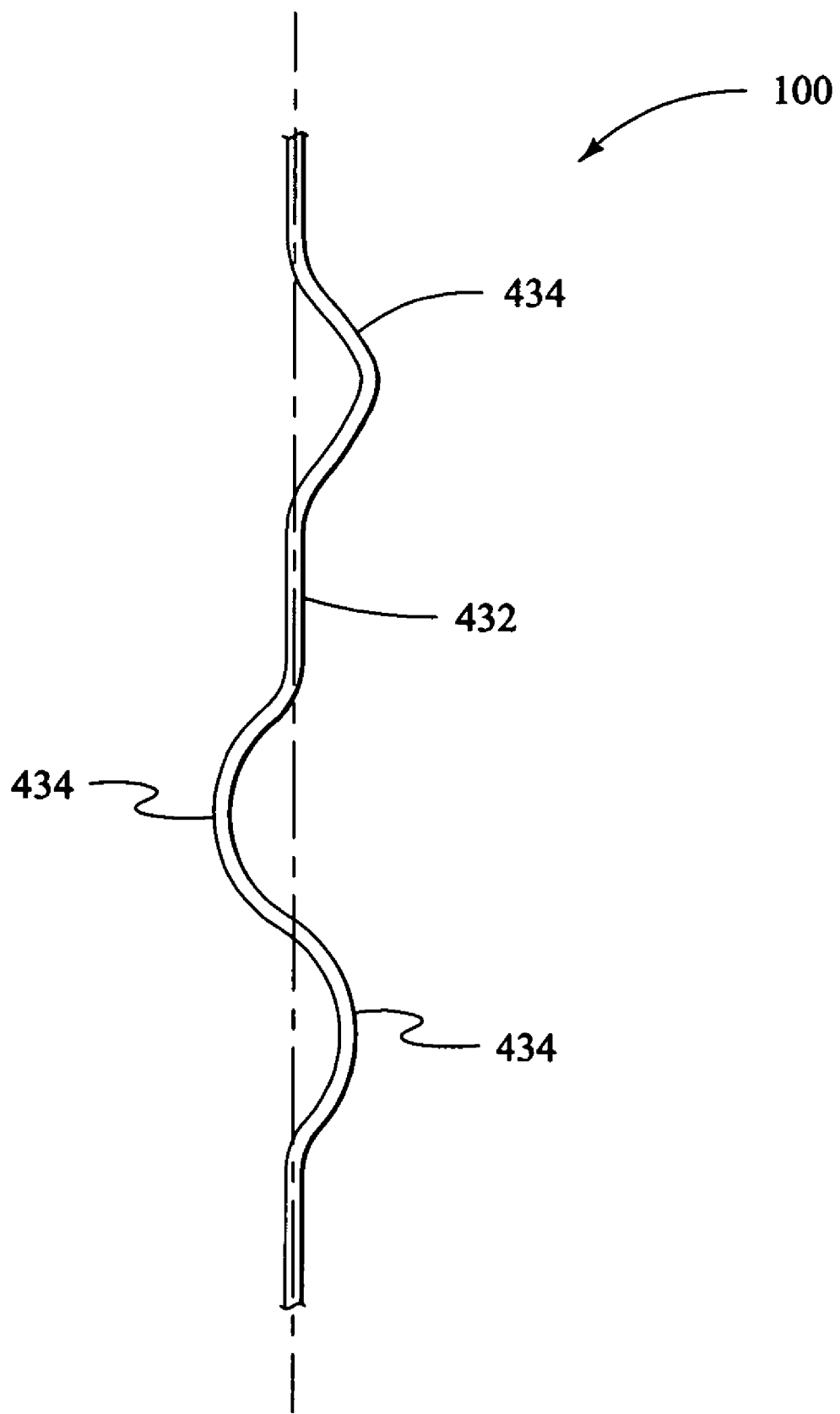

FIG. 10A shows another example of features useful to provide curves and complex shapes. In such embodiments, relatively flexible and inflexible sections of the articulator 100 can be provided by strengthening sections of the first wire rather than providing slots or resected portions. When a force is applied between the second wire and the first wire the articulator 100 will bend at the relatively flexible portions. For example, strengthened portions 420 can be provided along the articulator 100 (e.g., by welding or forming) as shown in FIG. 10A. In some embodiments, the first wire can comprise a plastic (such as, for example, silicone, urethane, polyamide, and combinations thereof) formed with relatively flexible and inflexible portions.

As shown in FIG. 10B, the distal ends can be provided with a relatively straight portion 432 distally and/or between curves 434. Such embodiments can be useful in navigating tortuous pathways and/or performing medical procedures. The relatively straight portion can be as long as desired.

Figure 11:
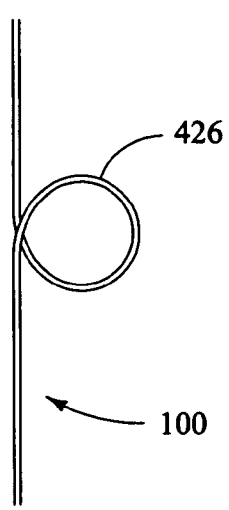
FIG. 11A provides a side plan view of an articulator in a curved shape in accordance with embodiments of the invention.
FIG. 11B provides a side plan view of an articulator in a curved shape in accordance with embodiments of the invention.
FIG. 11C provides a side plan view of an articulator in a curved shape in accordance with embodiments of the invention.
FIG. 11D provides a side plan view of an articulator in a curved shape in accordance with embodiments of the invention.
Figure 11:
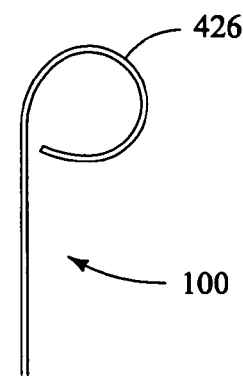
Figure 11:
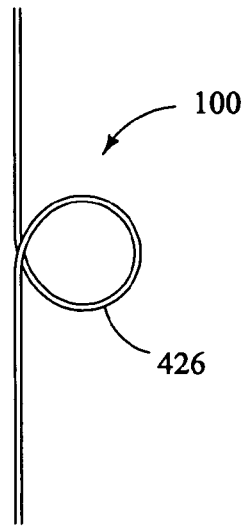
Figure 11:
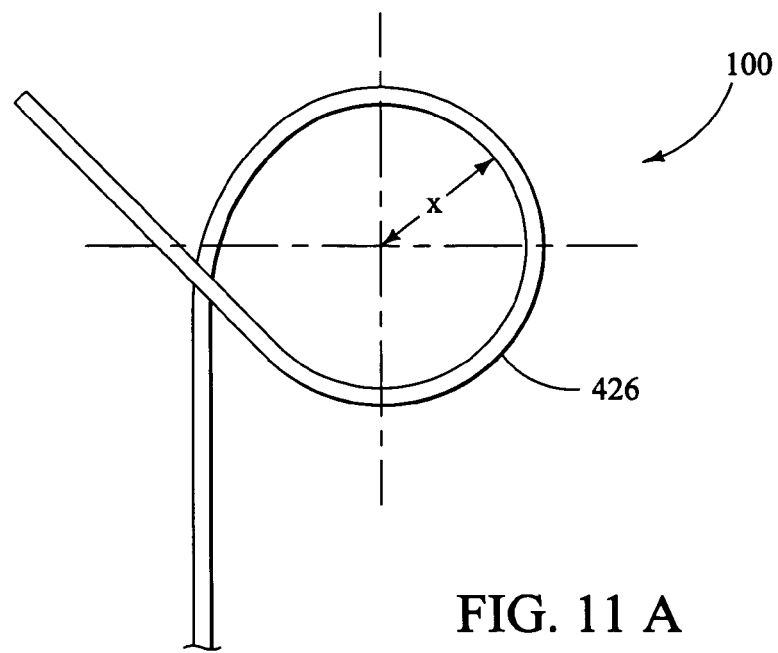

In some embodiments, as shown in FIG. 11A-D, a full circle bend 426 can also be created. The articulator 100 can terminate upon the completion of the full circle bend as shown in FIG. 11C, or it can have a distal portion extending beyond the full circle bend as shown in FIGS. 11B and D. Such embodiments can have about 100 to about 150 slots as described herein. As shown in the figures, the distal portion extending beyond the full circle bend can proceed in any desired direction and can be straight or curved.

Figure 12:
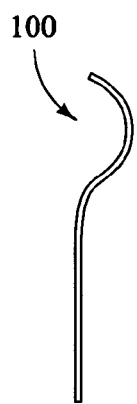
FIGS. 12A-L provides side plan views of an articulator in various curved shapes in accordance with embodiments of the invention.
FIG. 12M shows a perspective view of an articulator disposed within a vessel in accordance with embodiments of the invention.
Figure 12:
Figure 12:
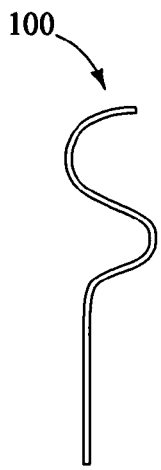
Figure 12:
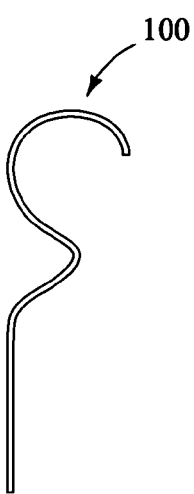
Figure 12:
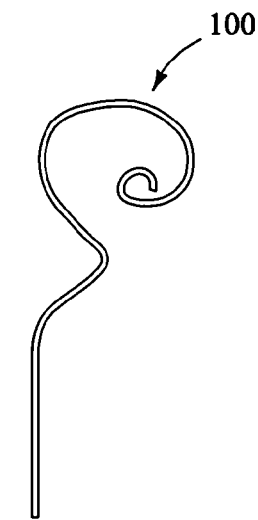
Figure 12:
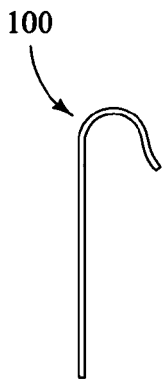
Figure 12:
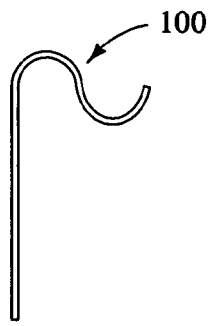
Figure 12:
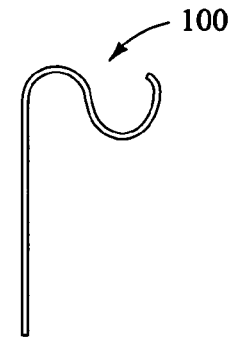
Figure 12:
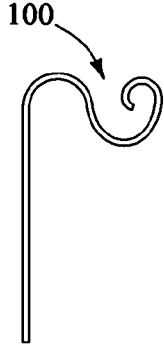
Figure 12:
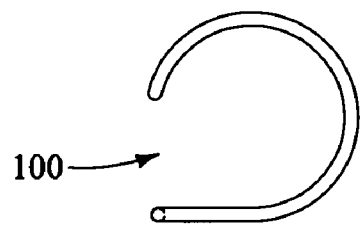
Figure 12:
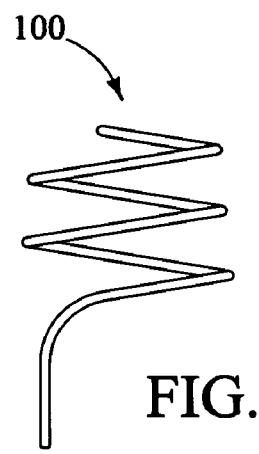
Figure 12:
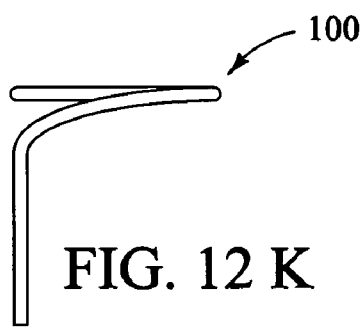
Figure 12:
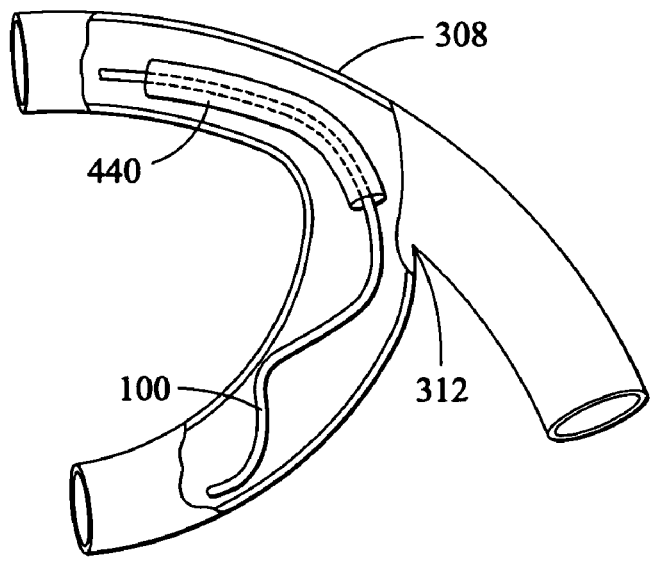

FIGS. 12A-L show several other representative complex curve patterns that can be provided using the methods described herein, including S-curves (FIGS. 12A-C), S-curves with additional distal curves (FIGS. 12D and E), C-curves with additional distal curves (FIGS. 12F-I), and helixes (FIGS. 12J-L). Such complex curves can be useful in navigating tortuous pathways and/or performing medical procedures. For example, the S-curves shown in FIGS. 12A-C can be particularly useful to access the coronary sinus from the ostium.

Some complex curves, including the helix curvatures shown in FIGS. 12J-L, can be used to anchor the articulator 100 to the wall of a vessel 308, as shown in FIG. 12M. In such an embodiment, the distal end of the articulator 100 can be navigated to a desired branch of a vessel 308 including, for example, a bifurcation 312. Once in the desired vessel the articulator 100 capable of helical curves can be placed in apposition with the vessel wall and turned to anchor it to the vessel wall. In some embodiments, the distal tip of the articulator 100 can be modified (e.g., sharpened) to facilitate such anchoring. The articulator 100 can then be utilized as a guidewire by routing a relatively stiffer medical device 440 (e.g., catheters and feeding tubes) over the articulator 100. Anchoring the articulator to the distal wall of the vessel helps prevent the relatively stiffer medical device from progressing into the undesired branch of the vessel at the bifurcation and dragging the articulator out of the desired branch. After the relatively stiffer medical device 440 has been routed into the desired branch of the vessel, the articulator can be turned to unfasten the articulator from the vessel wall. This process can be repeated as many times as necessary to route the catheter 440 to the desired location.

In some embodiments, the articulator can be provided with one or more enlarged portions 450, as shown in FIGS. 13A-C. Such enlarged portions 450 can extend substantially beyond the outer diameter of the first wire 102. Such enlarged portions can be adapted to provide a variety of functions. For example, in the embodiment shown in FIG. 13C, the enlarged portion 450 is located proximate the distal end of the articulator 100 and comprises a mesh 460 over one or more struts 462 to catch clots. Such an enlarged basket is useful for collecting and ultimately removing clots to reduce the chances of adverse medical procedure outcomes such as strokes. Further, such an enlarged basket is useful for collecting and removing stones (e.g., kidney or gall stones) from the body.

In the embodiment shown in FIG. 13A, enlarged portion 450 is also located proximate a distal portion of the articulator 100 and comprises a thin membrane (e.g., polymeric) attached to the spokes. When deployed in a tortuous pathway (e.g., the vascular system), the membrane acts as a passive occlusion device. Such devices have advantages over known occlusion devices, such as balloons. For example, no gasses or gas routing apparatus are required to deploy the device and the device can occlude a pathway using less pressure than an inflated balloon, thereby causing less damage to surrounding tissue.

Figure 14:
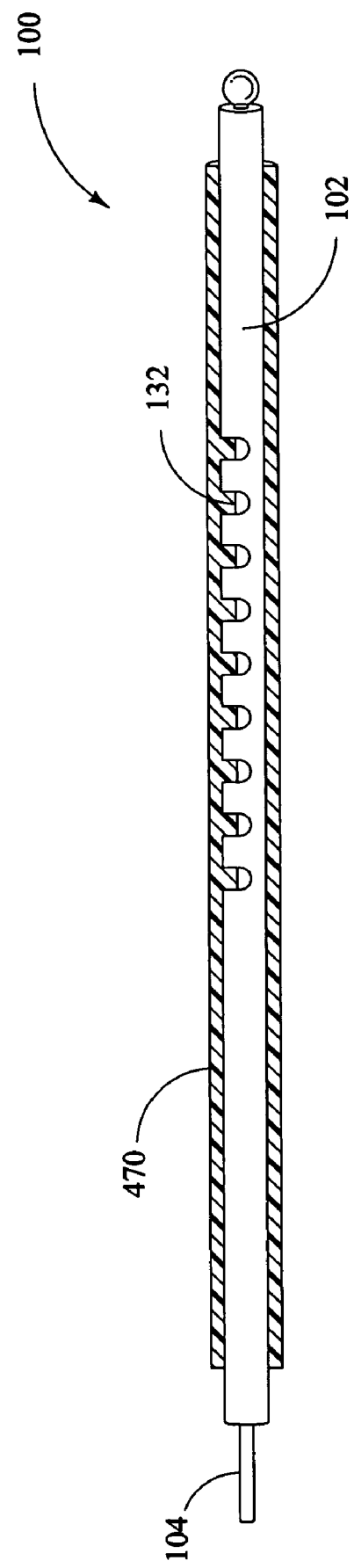
FIG. 14 provides a side plan view of an articulator with a coating in accordance with embodiments of the invention.

In some embodiments, the articulator 100 can be provided with a coating 470 as shown in FIG. 14. For example, with articulators having a first wire 102 and a second wire 104 as described above, a flexible coating 470 useful for shielding the articulator 100 from the fluids (e.g., bodily fluids), increasing lubricity, and/or increasing biocompatibility. Such coatings 470 can comprise any non-permeable materials such as, for example, silicone, urethane, polyamide, polytetrafluoroethylene (PTFE), polyester, and combinations thereof. Further, such a coating can be flexible enough to cover features such as slots 132 and resected portions without comprising the ability of the articulator 100 to articulate.

Figure 15:
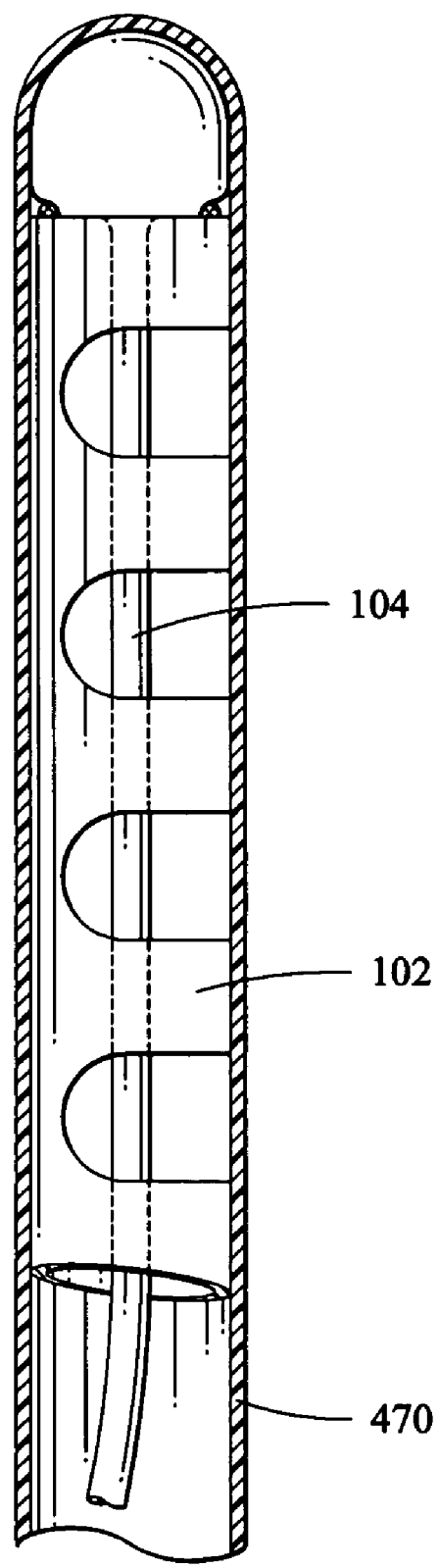
FIG. 15 provides a side plan view of an articulator with a coating in accordance with embodiments of the invention.
Figure 16:
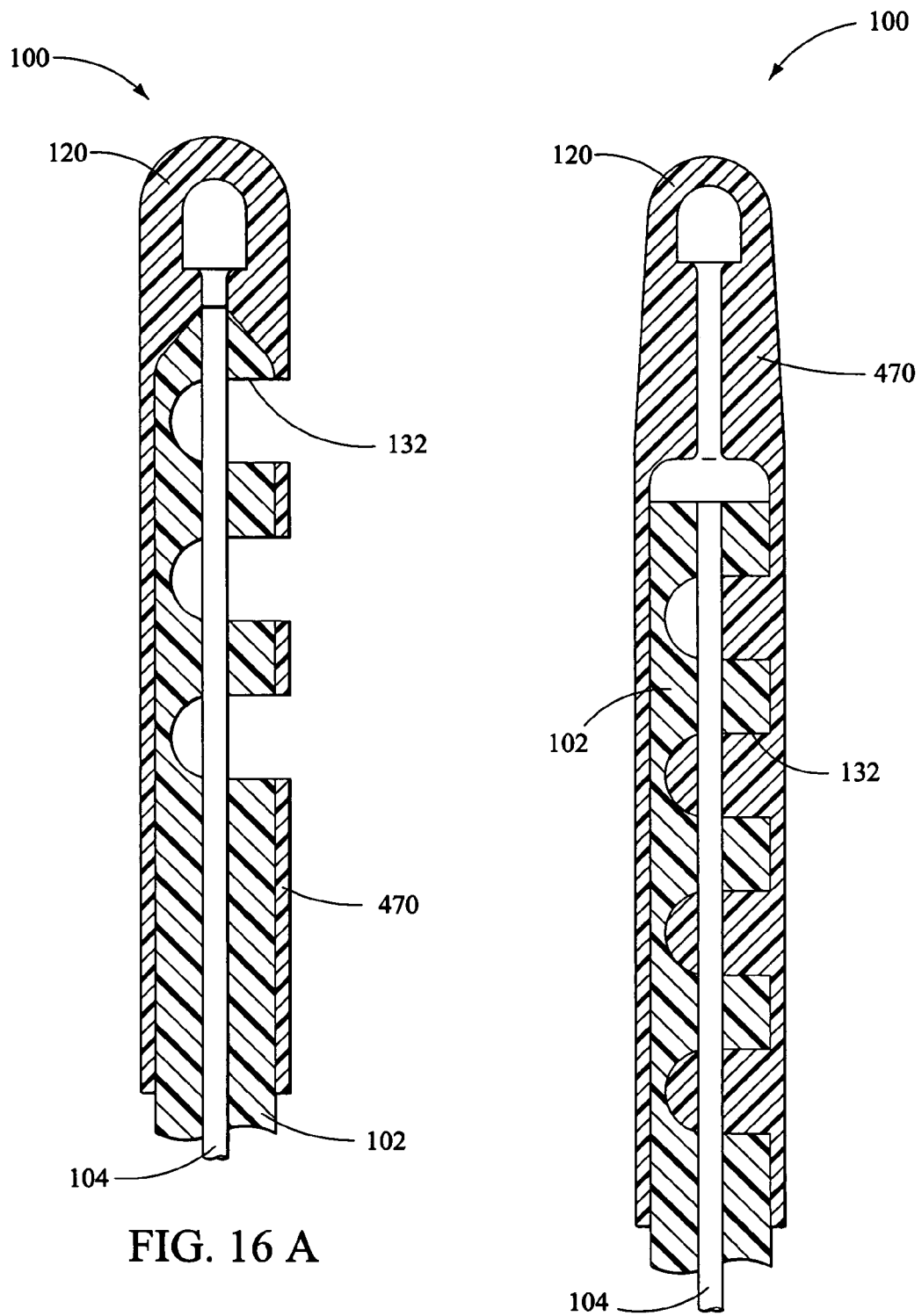
FIG. 16A provides a side plan view of an articulator with a coating in accordance with embodiments of the invention.
FIG. 16B provides a side plan view of an articulator with a coating in accordance with embodiments of the invention.

FIG. 15 shows a the distal end of an articulator 100 with a coating 470. As shown, such a coating can cover the distal end of the articulator 100. In some embodiments, the coating 470 provides an atraumatic distal end to reduce damage to the tortuous pathway as the articulator 100 is navigated through. Such coatings are useful for shielding relatively harder materials for the tortuous pathway and reducing adverse effects, such as thrombus. As shown in FIGS. 16A and B, the second wire 104 and first wire 102 can be shaped and connected to provide space for additional coating material about the distal end 120 of the articulator 100 to increase the atraumatic properties.

Figure 17:
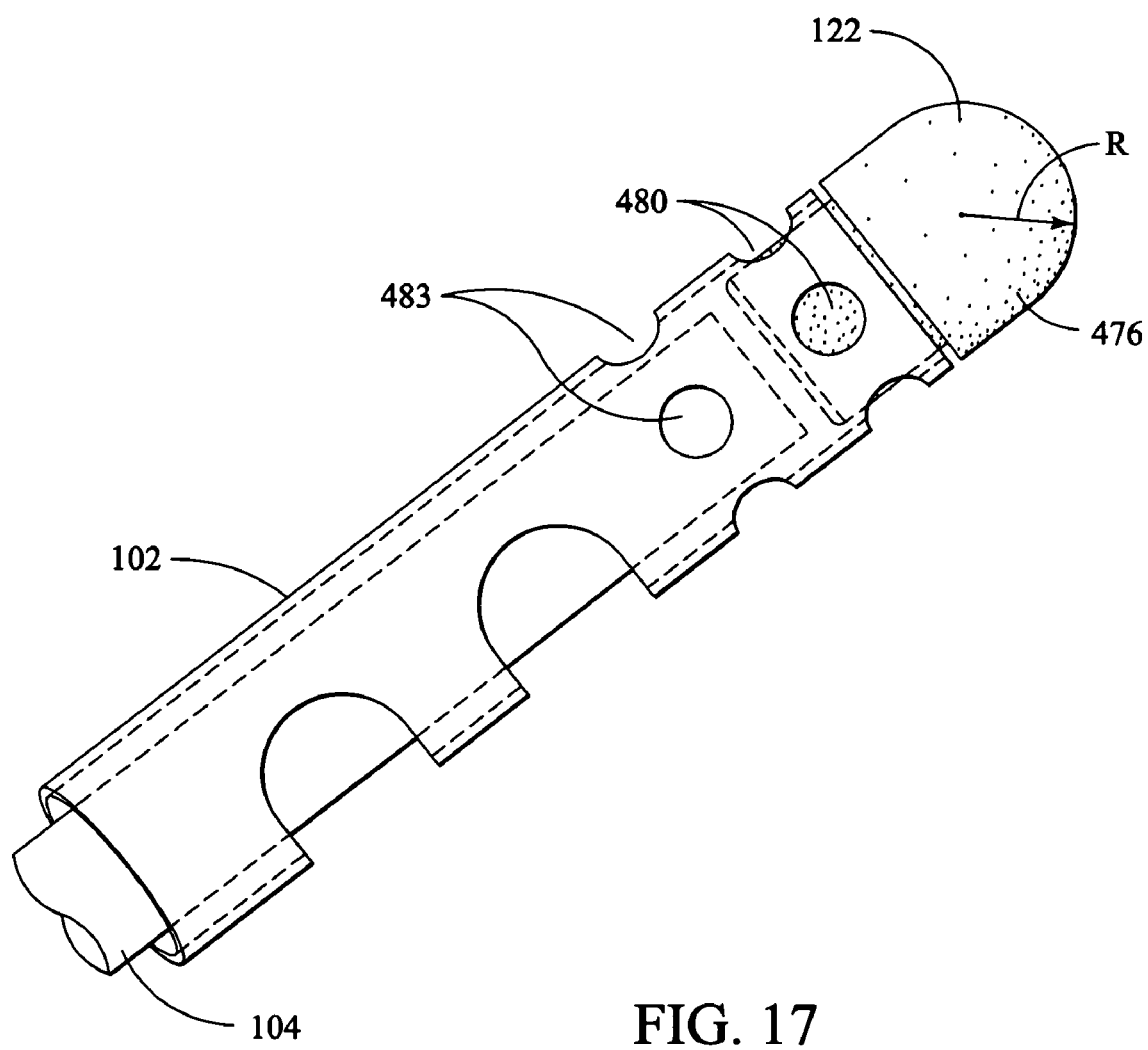
FIG. 17 provides a side plan view of an articulator with a soft distal tip in accordance with embodiments of the invention.

As shown in FIG. 17, a relatively soft distal tip 476 can be provided with or without a coating on the articulator 100. Such a soft distal tip 476 can comprise a polymer such as silicone, urethane, polyamide, PTFE, and combinations thereof. In some embodiments, the soft distal tip can comprise a radius R to further increase its atraumatic properties. As shown in FIG. 17, the second wire 104 and/or first wire 102 can be adapted to accommodate the soft distal tip. For example, tip apertures 480 can be provided in the first wire 102 to provide access for one or more bonding agents (e.g., an adhesive) to bond the soft distal tip to the articulator 100. First wire apertures 483 useful for providing access to attach the first wire to the second wire (e.g., by welding) can be provided proximally of the tip apertures 480.

Figure 18:
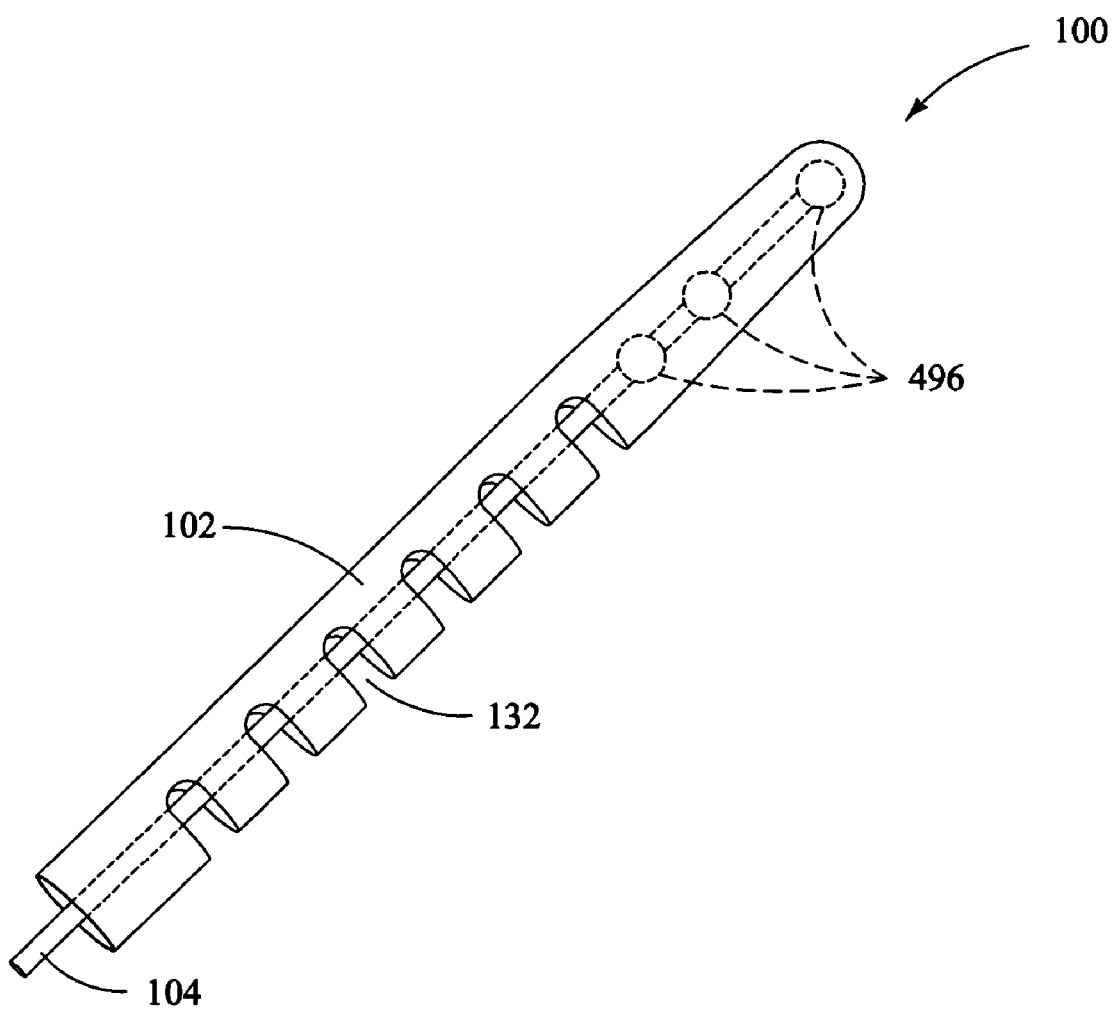
FIG. 18 provides a side plan view of an articulator with a polymeric wire in accordance with embodiments of the invention.

In some embodiments, the first wire itself can comprise a plastic with slots 132, as shown in FIG. 18. Such polymers can comprise materials such as silicone, urethane, polyamide, PTFE, and combinations thereof. The second wire 104 can be attached to such a first wire 102 as shown in FIG. 18. For example, the second wire 104 can contain one or more enlarged portions 496 adapted to couple it to a plastic cured around it.

Numerous characteristics and advantages of the invention covered by this document have been set forth in the foregoing description. It will be understood, however, that this disclosure is, in many respects, only illustrative. Changes can be made in details, particularly in matters of shape, size and ordering of steps without exceeding the scope of the invention. The invention's scope is, of course, defined in the language in which the appended claims are expressed.

What is claimed is:

1. An assembly including a handle for articulating an articulator, the handle comprising at least one accessible attachment mechanism useful for reattachably attaching the articulator and the handle during a medical procedure; and the handle further comprising:

a first portion axially aligned with a second portion;

a first actuating member pivotably coupled to the first portion and a second actuating member pivotably coupled to the second portion;

wherein the first and second actuating members are pivotably coupled to each other and configured such that squeezing the first and second actuating members toward the first and second portions of the handle causes the articulating of the articulator; and wherein the articulator comprises a first wire having a distal portion and a proximal portion and a second wire having a distal portion and a proximal portion, the second wire being disposed in a lumen defined by the first wire and the distal portion of the second wire being functionally coupled to the distal portion of the first wire.

2. An assembly according to claim 1, wherein the handle provides a one-to-one torqueability ratio.

3. An assembly according to claim 1, wherein the handle is adapted to navigate a distal end of the articulator through a tortuous pathway.

4. An assembly according to claim 1, wherein the handle comprises a biasing member to bias a distal end of the articulator to a desired position.

5. An assembly according to claim 4, wherein the biasing member comprises a spring.

6. An assembly according to claim 1, wherein the handle comprises a biasing member to bias a distal end of the articulator to a straight position.

7. An assembly according to claim 1, wherein the handle comprises a biasing member to bias a distal end of the articulator to a curved position.

8. An assembly according to claim 1, wherein the handle is adapted to lock a distal end of the articulator in a desired position.

9. An assembly according to claim 1, wherein the articulator includes a first wire and a second wire, the articulator having a distal end being articulatable by moving the first wire relative to the second wire.

10. An assembly according to claim 9, the handle adapted to move the first wire relative to the second wire by applying a longitudinal force differential between the first wire and the second wire.

11. An assembly according to claim 10, wherein the first portion is functionally coupled to a proximal portion of the first wire and the second portion is functionally coupled to a proximal portion of the second wire, the first and second portions being movable relative to each other.

12. An assembly according to claim 10, wherein the first portion is reattachably attached to the proximal portion of the first wire and the second portion is reattachably attached to the proximal portion of the second wire.

13. An assembly including a handle for articulating an articulator, the handle comprising at least one accessible attachment mechanism useful for reattachably attaching the articulator and the handle during a medical procedure; and the handle further comprising:
 a first portion axially aligned with a second portion;
 a first actuating member pivotably coupled to the first portion and a second actuating member pivotably coupled to the second portion;
 wherein the first and second actuating members are pivotably coupled to each other and configured such that squeezing the first and second actuating members toward the first and second portions of the handle causes the articulating of the articulator;
 wherein the articulator includes a first wire and a second wire, the articulator having a distal end being articulatable by moving the first wire relative to the second wire, the handle adapted to move the first wire relative to the second wire by applying a longitudinal force differential between the first wire and the second wire;
 wherein the first portion is reattachably attached to the proximal portion of the first wire and the second portion is reattachably attached to the proximal portion of the second wire; and
 wherein the first portion is reattachably attached to the first wire by a first collet and a first collet nut, and the second portion is reattachably attached to the second wire by a second collet and a second collet nut.

14. An assembly according to claim 13, wherein the handle has a proximal end and a distal end, the first collet and first collet nut being proximate the proximal end and the second collet and second collet nut being proximate the distal end to provide easy access for detaching and reattaching the articulator and the handle.

15. An assembly according to claim 1, wherein the first and second actuating members are useful for actuating the articulation of a distal end of the articulator.

16. An assembly according to claim 1, wherein the articulator comprises a plurality of notches.

17. An assembly according to claim 1, wherein the articulator has an adjustable stiffness.

18. An assembly according to claim 1, wherein the articulator has an adjustable length.

19. An assembly according to claim 1, the handle being able to deflect a distal portion of the articulator when squeezed.

20. An assembly according to claim 1, wherein the first portion of the handle is adapted to be engaged by one or both of the thumb and the palm of a human hand.

21. An assembly according to claim 1, wherein the first actuating member of the handle is adapted to engaged by one or both of the index and middle fingers of the human hand.

22. An assembly according to claim 14, wherein the handle has a stop to keep the first wire from exiting the handle.

23. An assembly according to claim 1, further comprising the articuluator reattachably attached to the handle.

24. An assembly according to claim 23, wherein the articulator is steerable.

25. An assembly according to claim 12, wherein the articulator has one or more of an adjustable length and stiffness.

26. An assembly according to claim 23, wherein the articulator is steerable and has one or more of an adjustable length and stiffness.

27. An assembly according to claim 23, wherein the articulator comprises a first wire with a first feature longitudinally offset from a second feature to provide relatively complex articulator shapes.

28. An assembly according to claim 27, wherein the first and second features independently comprise notches, resected portions, and/or strengthened portions.

29. An assembly according to claim 23, wherein the articulator comprises an enlarged distal end.

30. An assembly according to claim 29, wherein the enlarged distal end comprises a basket useful for collecting clots.

31. An assembly according to claim 29, wherein the enlarged distal end comprises a membrane useful for occluding a tortuous pathway.

32. An assembly according to claim 23, further including a coating provided over at least the distal end of the articulator.

33. An assembly according to claim 23, wherein the articulator comprises an atraumatic distal tip.

34. An assembly according to claim 23, wherein the articulator comprises a second wire disposed within a lumen defined by a first wire, the first wire comprising a polymer.

35. A handle for articulating an articulator, the handle comprising:
 at least one accessible attachment mechanism useful for reattachably attaching the articulator and the handle during a medical procedure, the handle being able to deflect a distal portion of the articulator when squeezed;
 a first portion axially aligned with a second portion;
 a first actuating member pivotably coupled to the first portion and a second actuating member pivotably coupled to the second portion;

wherein the first and second actuating members are pivotably coupled to each other and configured such that squeezing the first and second actuating members toward the first and second portions of the handle causes deflection of the distal portion of the articulator; and wherein the articulator comprises a first wire having a distal portion and a proximal portion and a second wire having a distal portion and a proximal portion, the second wire being disposed in a lumen defined by the first wire and the distal portion of the second wire being functionally coupled to the distal portion of the first wire.

36. An assembly comprising:
an articulator comprising proximal and distal end portions, and a corresponding handle, the articulator and handle being adapted to be mated at the proximal end portion, in order to permit the resulting assembly to be operated;
the handle further comprising:
a first portion axially aligned with a second portion; and
a first actuating member pivotably coupled to the first portion and a second actuating member pivotably coupled to the second portion;
wherein the first and second actuating members are pivotably coupled to each other and configured such that squeezing the first and second actuating members toward the first and second portions of the handle causes deflection of the distal portion of the articulator; and
wherein the articulator comprises a first wire having a distal portion and a proximal portion and a second wire having a distal portion and a proximal portion, the second wire being disposed in a lumen defined by the first wire and the distal portion of the second wire being functionally coupled to the distal portion of the first wire.

37. The assembly of claim 36, wherein the articulator can be releasably mated with the handle.

38. The assembly of claim 36, wherein the assemble is configured for single-handed operation.

39. The assembly of claim 36, wherein the articulator can be releasably mated with the handle.

40. The assembly of claim 36, wherein the distal end of the articulator can be controlled so as to form a plurality of desired shapes.

41. The assembly of claim 40, wherein the distal end provides a non-traumatic distal end.

42. The assembly of 36, wherein the assembly adapted to control the movement of the articulator in a desired manner within a three dimensional coordinate system, including X, Y and Z axes corresponding to the X dimension, linearly (in a proximal-distal direction), the Y dimension, radially, emanating from the core of the articulator, and the Z dimension, in a generally concentric dimension, as by rotating around the central axis of the articulator.

43. The assembly of claim 42, wherein the assembly can be operated to provide a controlled array of distal end portion forms that include straight, bends; curves and combinations thereof.

44. The assembly of claim 36, wherein the articulator operates on a "push-pull" basis that involves the use of relative motion as between a plurality of parts.

45. The assembly of claim 44, wherein the parts comprise a core wire and an adjacent or surrounding stylet or guidewire.

46. The assembly of claim 36, wherein the single handed fashion comprises finger operation and hand movement such as turning and/or advancing.

* * * * *